US012721832B2

(12) United States Patent
Sun et al.

(10) Patent No.: US 12,721,832 B2
(45) Date of Patent: Sep. 1, 2026

(54) ANTI-SENESCENCE PLANT POLYPHENOL DRUG DOWNREGULATING SENESCENCE-RELATED SECRETORY PHENOTYPE AND USE THEREOF

(71) Applicant: BYHEALTH CO., LTD., Zhuhai (CN)

(72) Inventors: Yu Sun, Shanghai (CN); Qixia Xu, Shanghai (CN); Xuguang Zhang, Guangzhou (CN); Ruikun He, Guangzhou (CN)

(73) Assignee: BYHEALTH CO., LTD., Zhuhai (CN)

( * ) Notice: Subject to any disclaimer, the term of this patent is extended or adjusted under 35 U.S.C. 154(b) by 424 days.

(21) Appl. No.: 18/262,319

(22) PCT Filed: Feb. 23, 2021

(86) PCT No.: PCT/CN2021/077495

§ 371 (c)(1),
(2) Date: Jul. 20, 2023

(87) PCT Pub. No.: WO2022/165868

PCT Pub. Date: Aug. 11, 2022

(65) Prior Publication Data

US 2024/0091193 A1 Mar. 21, 2024

(30) Foreign Application Priority Data

Feb. 4, 2021 (CN) ......................... 202110156372.3

(51) Int. Cl.

*A61K 31/353* (2006.01)
*A61K 31/352* (2006.01)
*A61K 31/425* (2006.01)
*A61K 31/704* (2006.01)
*A61P 35/00* (2006.01)

(52) U.S. Cl.

CPC .......... *A61K 31/353* (2013.01); *A61K 31/352* (2013.01); *A61K 31/425* (2013.01); *A61K 31/704* (2013.01); *A61P 35/00* (2018.01)

(58) Field of Classification Search

CPC .. A61K 31/353; A61K 31/352; A61K 31/425; A61K 31/704; A61P 35/00
See application file for complete search history.

(56) References Cited

U.S. PATENT DOCUMENTS 5,891,905 A 4/1999 Romanczyk, Jr. et al.
2004/0220392 A1 11/2004 Romanczyk, Jr. et al.
2008/0260695 A1 10/2008 Lu

FOREIGN PATENT DOCUMENTS

CN 1654462 A 8/2005
CN 102300578 A 12/2011
CN 110478488 A 11/2019
JP H10506903 A 7/1998
WO 1996010404 A1 4/1996
WO 2002067965 A1 9/2002

OTHER PUBLICATIONS

Sharma, G. et al. Synergistic anti-cancer effects of grape seed extract and conventional cytotoxic agent doxorubicin against human breast carcinoma cells. Breast Cancer Res Treat 2004, 85, 1-12. (Year: 2004).*
Wolff, et al. Burger's Medicinal Chemistry and Drug Discovery. 5th Ed. Part 1, 1995. p. 975-977. (Year: 1995).*
Banker, G. S. Modern Pharmaceutics, 3rd ed. 1996. p. 596. (Year: 1996).*
Zhang, X.-Y. et al. Proanthocyanidin from grape seeds potentiates anti-tumor activity of doxorubicin via immunomodulatory mechanism. International Immunopharmacology 2005, 5, 1247-1257. (Year: 2005).*
Köhler et al., "Preparative isolation of procyanidins from grape seed extracts by high-speed counter-current chromatography." Journal of Chromatography A 1177(1): 114-125 (2008).
Lin et al., "Grape seed proanthocyanidin extract reverses multidrug resistance in HL-60/ADR cells via inhibition of the PI3K/Akt signaling pathway." Biomedicine & Pharmacotherapy 125:109885 (2020).
Yu et al., "Anticancer activities of proanthocyanidins from the plant Urceola huaitingii and their synergistic effects in combination with chemotherapeutics." Fitoterapia 112: 175-182 (2016).
International Search Report issued Nov. 10, 2021 in corresponding International Patent Application No. PCT/CN2021/077495 (English Translation).
Neuwirt et al., Oligomeric proanthocyanidin complexes (OPC) exert anti-proliferative and pro-apoptotic effects on prostate cancer cells, The Prostate, 2008, 68:1647-1654.
Zhang et al., Research progress on anti-tumor effect and mechanism of Proanthocyanidin, Chongqing Medicine, 2012, 41(27):2887-2889. (with English Abstract).
Zhang et al., Proanthocyanidin from grape seeds enhances anti-tumor effect of doxorubicin both in vitro and in vivo, Pharmazie, 2005, 60:533-538.

(Continued)

*Primary Examiner* — Jeffrey H Murray
*Assistant Examiner* — Kristen W Romero
(74) *Attorney, Agent, or Firm* — Medler Ferro Woodhouse & Mills PLLC

(57) ABSTRACT

Disclosed is a pharmaceutical composition containing (a) procyanidin or pharmaceutically acceptable salt, hydrate or prodrug thereof, and (b) a reagent capable of inducing an object to generate senescent cells, and optionally, a pharmaceutically acceptable excipient, where the procyanidin is procyanidin C1 and the reagent is mitoxantrone (MIT). Disclosed is the use of the procyanidin or the pharmaceutically acceptable salt, hydrate or prodrug thereof and the pharmaceutical composition in the preparation of a drug or preparation for use in reducing drug tolerance to cancer therapy, enhancing the efficacy of the reagent capable of inducing cell senescence, promoting tumor regression, reducing tumor volume, preventing or treating cancers, or prolonging cancer survival, especially for prostate cancer or tumors.

4 Claims, 18 Drawing Sheets

Specification includes a Sequence Listing.

(56) References Cited

OTHER PUBLICATIONS

Byun, Eui-Baek et al., "A Procyanidin Trimer, C1, Promotes NO Production in Rat Aortic Endothelial Cells via both Hyperpolarization and PI3K/Akt Pathways", European Journal of Pharmacology 692: 52-60 (2012).
Shang et al., "Procyanidin induces apoptosis and necrosis of prostate cancer cell line PC-3 in a mitochondrion-dependent manner," *Journal of Andrology* 30(2):122-126 (2009).

* cited by examiner

ANTI-SENESCENCE PLANT POLYPHENOL DRUG DOWNREGULATING SENESCENCE-RELATED SECRETORY PHENOTYPE AND USE THEREOF

SEQUENCE LISTING

The instant application contains a Sequence Listing which has been submitted electronically in ASCII format and is hereby incorporated by reference in its entirety. Said ASCII copy, created on Jul. 20, 2023, is named IEC232051PUS_ST25.txt and is 5,360 bytes in size.

TECHNICAL FIELD

The present application belongs to the field of biomedicine, and more specifically, the present application relates to an anti-senescence drug for downregulating or clearing senescent cells and uses thereof.

BACKGROUND ART

Cell senescence refers to a usually stable and essentially irreversible state of cell cycle arrest in eukaryotic cells, in which proliferating cells become resistant to growth-promoting stimuli, mostly induced by stress signals such as DNA damage. Senescent cells are characterized by abnormal morphology, altered metabolic activity, chromatin remodeling, aberrant gene expression, increased lipofuscin, enhanced granularity, severe vacuolization, and a senescence-associated secretory phenotype (SASP) pro-inflammatory phenotype. The biological role of senescence is highly complex, and both protective effects and deleterious effects of senescent cells have been described, mainly depending on the pathophysiological environment. For example, although senescence may have evolved as a mechanism to avoid malignant transformation of damaged cells, the occurrence of senescence may lead to many age-related pathologies, including a series of clinical problems such as cancer, cardiovascular and cerebrovascular diseases, osteoporosis, arthritis, metabolic diseases, neurological degenerative symptoms.

Cell senescence is characterized by infolding of nuclear membrane, chromatin condensation, increased cell volume, activation of multiple downstream signaling pathways including p53, $p16^{INK4A}$/Rb, P13K/Akt, FoxO transcription factors, and mitochondrial SIRT1. In addition to entering permanent proliferative arrest, senescent cells are often associated with many pathological features, including local inflammation and tissue degradation. Cell senescence occurs in damaged cells and prevents them from proliferating in an organism. Under the influence of various external stimuli and internal factors, cell damage can lead to obvious signs of cell senescence. When the accumulation of damage reaches a certain limit, various tissue degenerative changes and physiological senescence phenotypes can be discerned in the tissue level.

Particularly, the most noteworthy feature is the significantly increased expression of inflammatory cytokines by senescent cells, a phenomenon known as the senescence-associated secretory phenotype (SASP). The concept of SASP was first proposed by Coppe et al. in 2008. They found that senescent cells can promote the proliferation of adjacent precancerous cells or increase the malignancy of cancer cells by secreting extracellular matrix proteins, inflammation-related factors and cancer cell growth factors, and collectively referred to as SASP factors'.

Although various SASP inhibitors known internationally can significantly weaken SASP, they can not kill senescent cells in essence. In order to reduce the burden of senescent cells pharmacologically, scientists are developing small molecules, peptides and antibodies, together known as "senolytics" (senescent cell-eliminating drugs) to selectively kill senescent cells. Since the discovery of senolytic drugs in 2015, researchers have made considerable progress in identifying other small molecule senolytic drugs and clarifying their actions. Numerous studies have shown that most senolytics are only effective on a limited number of senescent cell types. For example, Navitoclax is able to target HUVECs but not senescent human preadipocytes. Evidence suggests that the efficacy of senolytics may vary even within one specific cell type. For example, in human lung fibroblasts, Navitoclax can target and kill senescent cells in culture-adapted IMR90 fetal lung fibroblast-like cell lines, but is less effective in senescent primary human lung fibroblasts.

Therefore, there is still a need to find more effective anti-senescence drugs with a wider range of application in this field.

Contents of the Invention

The first aspect of the present application provides a pharmaceutical composition, comprising a procyanidin or a pharmaceutically acceptable salt, hydrate or prodrug thereof, and an optional pharmaceutically acceptable auxiliary material.

In one or more embodiments, the procyanidin is an oligomeric procyanidin, preferably comprising procyanidin C1.

In one or more embodiments, in the pharmaceutical composition, the procyanidin or pharmaceutically acceptable salt, hydrate or prodrug thereof has a final concentration of at least 1 μM, such as at least 1 μM, at least 10 μM, at least 20 μM, at least 30 μM, at least 40 μM, at least 50 μM, at least 100 μM, at least 200 μM, at least 500 μM, at least 1 mM, or in a range between any two values above.

In one or more embodiments, the pharmaceutical composition further comprises an agent capable of inducing a subject to produce a senescent cell.

In one or more embodiments, the agent is capable of inducing production of a senescent cell in a tumor tissue.

In one or more embodiments, the agent is capable of causing DNA damage and/or apoptosis, for example, DNA double strand breaks.

In one or more embodiments, the agent is MIT or DOX.

The present application also provides a use of a procyanidin or a pharmaceutically acceptable salt, hydrate or prodrug thereof in the manufacture of a medicament or preparation, and the medicament or preparation is used for: downregulating a senescence-associated secretory phenotype (SASP), reducing expression or activity of a SASP factor, reducing expression or activity of a cell senescence marker factor, inducing apoptosis of a non-proliferating cell, reducing or eliminating a non-proliferating cell, delaying senescence, prolonging lifespan of a subject, reducing an age-related disease burden in a subject, preventing, alleviating and treating a disease benefiting from the reduction or elimination of non-proliferating cells, reducing resistance to a cancer therapy, enhancing efficacy of an agent capable of inducing cell senescence, promoting tumor regression, reducing tumor size, preventing or treating a cancer, or prolonging cancer survival.

In one or more embodiments, the procyanidin is an oligomeric procyanidin, preferably comprising procyanidin Cl.

In one or more embodiments, the SASP factor comprises an extracellular matrix protein, an inflammatory cytokine, and a cancer cell growth factor.

In one or more embodiments, the SASP factor comprises a factor as shown in FIG. 6.

In one or more embodiments, the SASP factor is selected from a group of molecules consisting of: IL6, CXCL8, MCP2, CXCL1, GM-CSF, MMP3, AREG, SFRP2, ANGPTL4, IL1a.

In one or more embodiments, the cell senescence marker factor is selected from a group consisting of: $p16^{INK4a}$, $p21^{CIP1}$.

In one or more embodiments, the non-proliferating cell is a senescent cell, such as a naturally senescent cell or a damaged cell. The damaged cell comprises a damaged cell in a tissue microenvironment, preferably a damaged cell caused by chemotherapy or radiation therapy. In one or more embodiments, the radiation therapy comprises: ionizing radiation, $\alpha$ radiation therapy, $\beta$ radiation therapy or $\gamma$ radiation therapy.

In one or more embodiments, the disease benefiting from reduction or elimination of a non-proliferating cell is an age-related disease, including but not limited to cancer, cardiovascular and cerebrovascular disease, osteoporosis, age-related degenerative joint disease (e.g., arthritis), metabolic disease, neurodegenerative disease. Preferably, the cancer is a prostate cancer; the tumor is a prostate tumor.

In one or more embodiments, the agent capable of inducing cell senescence comprises an agent that causes DNA damage and/or apoptosis, such as a chemotherapeutic agent or radiation. Preferably, the reagent comprises MIT or DOX.

In one or more embodiments, the subject is an elderly subject. In specific embodiments, the elderly subject is a subject corresponding to a mouse of at least 20 months of age or a human of at least 60 years of age. Preferably, the elderly subject is a subject corresponding to a mouse of at least 24 months of age or a human of at least 75 years of age. More preferably, the elderly subject is a subject corresponding to a mouse of 24 to 27 months of age or a human of 75 to 90 years of age.

In one or more embodiments, the cancer therapy comprises chemotherapy or radiation therapy, for example, MIT therapy, DOX therapy, ionizing radiation, $\alpha$ radiation therapy, $\beta$ radiation therapy or $\gamma$ radiation therapy.

The present application also provides a use of (a) a procyanidin or a pharmaceutically acceptable salt, hydrate or prodrug thereof, and (b) an agent capable of inducing a subject to produce a senescent cell in the manufacture of a medicament or preparation, the medicament or preparation is used for: promoting tumor regression, reducing tumor volume, preventing or treating a cancer, prolonging cancer survival.

In one or more embodiments, the procyanidin is an oligomeric procyanidin, preferably comprising procyanidin C1.

In one or more embodiments, the agent is capable of inducing the generation of a senescent cell in a tumor tissue.

In one or more embodiments, the agent is capable of causing DNA damage and/or apoptosis, for example, DNA double strand breaks.

In one or more embodiments, the agent is MIT or DOX.

In one or more embodiments, (a) is capable of eliminating a senescent cell.

In one or more embodiments, the tumor is a prostate tumor; the cancer is a prostate cancer.

Another aspect of the present application provides a medicinal box or kit, which comprises the pharmaceutical composition described in the first aspect herein and an optional agent capable of inducing a subject to produce a senescent cell.

In one or more embodiments, the medicinal box or kit comprises Container 1 and Container 2, which respectively contain (a) a procyanidin or a pharmaceutically acceptable salt, hydrate or prodrug thereof and an optional pharmaceutically acceptable auxiliary material, and (b) an agent capable of inducing a subject to produce a senescent cell and an optional pharmaceutically acceptable auxiliary material.

In one or more embodiments, in the pharmaceutical composition, the medicinal box or the kit, (a) and optional (b) are used as active ingredients, and other ingredients are pharmaceutically acceptable auxiliary material and the like.

In one or more embodiments, a dosage form of the pharmaceutical composition comprises: oral agent, injection, infusion solution, tablet, powder, capsule, pill; and the preferred dosage form is oral agent.

In another aspect of the present application, there is provided a method for causing a change in a non-proliferating cell or a subject, the method comprising treating the non-proliferating cell with a procyanidin or pharmaceutically acceptable salt, hydrate or prodrug thereof or administrating the same to the subject, in which the change comprises one or more selected from the following: down-regulating senescence-associated secretory phenotype (SASP), reducing expression or activity of a SASP factor, reducing expression or activity of a cell senescence marker factor, inducing apoptosis of a non-proliferating cell, reducing or eliminating a non-proliferating cell, delaying senescence, prolonging lifespan of a subject, reducing an age-related disease burden in a subject, preventing, alleviating and treating a disease that can benefit from the reduction or elimination of a non-proliferating cell, enhancing cytotoxicity of an agent capable of inducing cell senescence, or reducing resistance to a cancer therapy.

In one or more embodiments, the procyanidin or pharmaceutically acceptable salt, hydrate or prodrug thereof has a final concentration of at least 1 μM, such as at least 10 μM, at least 20 μM, at least 30 μM, at least 40 μM, at least 50 μM, at least 100 μM, at least 200 μM, at least 500 μM, at least 1 mM, or in a range between any two values above.

In one or more embodiments, the procyanidin is an oligomeric procyanidin, preferably comprising procyanidin C1.

Another aspect of the present application provides a method for enhancing cytotoxicity of an agent capable of inducing cell senescence, promoting tumor regression, reducing tumor volume, preventing or treating cancer, or prolonging cancer survival, the method comprises using (a) a procyanidin or pharmaceutically acceptable salt, hydrate or prodrug thereof, and (b) an agent capable of inducing a subject to produce senescent cell in treating a cell or administering the same to the subject.

In one or more embodiments, the procyanidin is an oligomeric procyanidin, preferably comprising procyanidin C1.

In one or more embodiments, the agent is capable of inducing the generation of a senescent cell in a tumor tissue.

In one or more embodiments, the agent is capable of causing DNA damage and/or apoptosis, for example, DNA double strand breaks.

In one or more embodiments, the agent is MIT or DOX.

In one or more embodiments, the tumor is a prostate tumor; the cancer is a prostate cancer.

In one or more embodiments, the procyanidin or pharmaceutically acceptable salt, hydrate or prodrug thereof has a final concentration of at least 10 μM, such as at least 20 μM, at least 30 μM, at least 40 μM, at least 50 μM, at least 100 μM, at least 200 μM, at least 500 μM, at least 1 mM, or in a range between any two values above.

In one or more embodiments, the use or method described in any of the embodiments herein is not directly aimed at the treatment of a clinical disease.

Other aspects of the present application will be apparent to those skilled in the art from the disclosure herein.

SPECIFIC MODELS FOR CARRYING OUT THE APPLICATION

Figure 1:
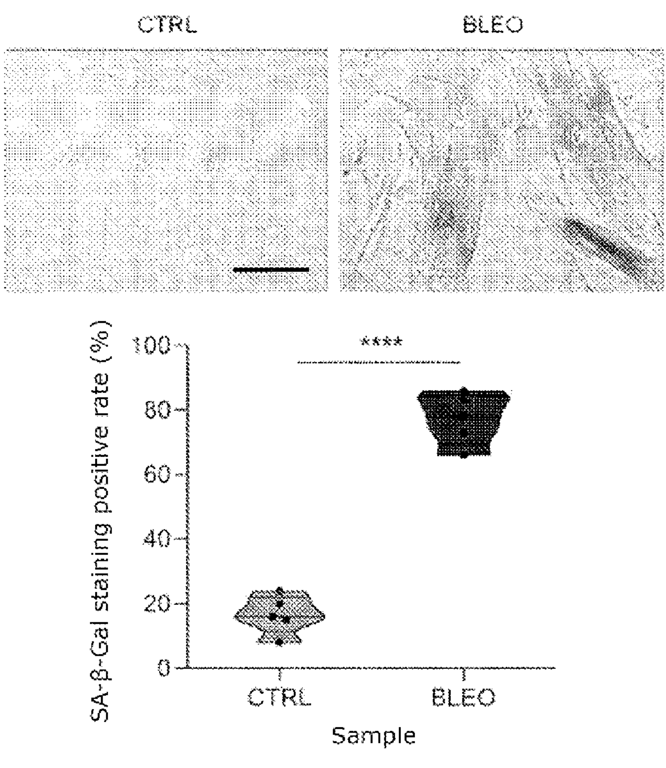
FIG. 1 shows the results of SA-β-Gal staining of proliferating human stromal cells PSC27 (early passages: such as p10-20) 7-10 days after they were in vitro treated with chemotherapeutic drug bleomycin (BLEO) at a concentration of 50 μg/ml, in which the upper part shows representative images, and lower part shows statistical data. CTRL, control cells; BLEO, cells treated with bleomycin. **, P<0.01.

The inventors found that procyanidins have an excellent effect on downregulating or clearing senescent cells in the body, so it can be applied to clear damaged cells in the tissue microenvironment, and can also be used to clear cells that naturally age with the increased age.

As used in the present application, “proliferating cell” refers to a cell that can maintain a state of continuous and active division and continuous proliferation. “Non-proliferating cell” in a narrow sense refers to a senescent cell, such as a naturally senescent cell or a damaged cell, and the damaged cell includes a damaged cell in the tissue microenvironment, preferably a damaged cell caused by chemotherapy or radiation therapy. As used in the present application, “senescent cell” refers to a cell whose ability of proliferation and division is reduced, and whose physiological function declines.

The “procyanidin” mentioned herein is a general term for polyphenolic compounds, including oligomeric procyanidin. Procyanidin are an important class in the plant polyphenol family. Most of this flavanol compounds are formed by linking catechin or epicatechin through the C4-C6 and C4-C8 of the flavan bond, and some of the compounds are gallate; their commonality is that they are oligomers composed of anthocyanin monomers in essence, mostly dimers and trimers. Exemplary oligomeric procyanidins have units represented by Formula I, the number of units is greater than 1 to 6, wherein the wavy lines represent connections with other units.

(I)

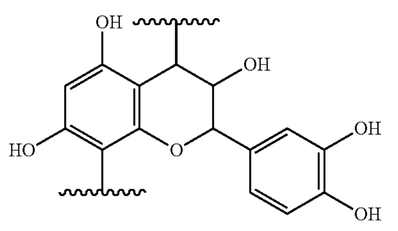

In some embodiments, the procyanidin is procyanidin C1 (PCC1) represented by the following Formula:

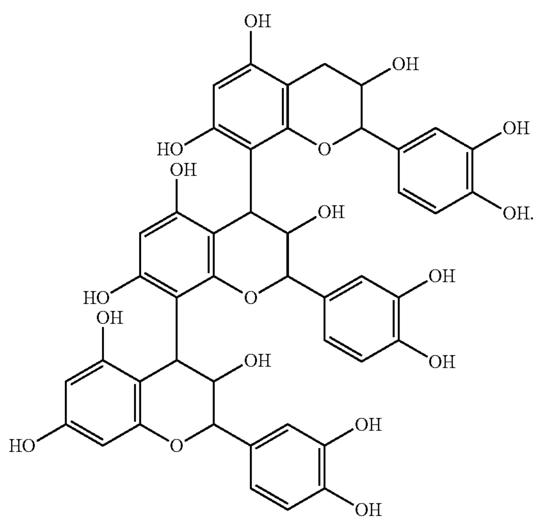 [SMILES: Oc1cc(O)c2c(c1)OC(c1ccc(O)c(O)c1)C(O)C2c1c(O)cc(O)c2c1OC(c1ccc(O)c(O)c1)C(O)C2c1c(O)cc(O)c2c1OC(c1ccc(O)c(O)c1)C(O)C2]

PCC1 is a trimer in the plant polyphenol family, and it not only has anti-oxidation, anti-inflammatory, anti-cancer effects, but also has the function of targeting and clearing senescent cells.

In the present application, “compound” (including procyanidin, salt or prodrug thereof, etc.) can be a compound in pure form, or a compound with a purity greater than 85% (preferably greater than 90%, such as 95%, 98%, 99%).

Those skilled in the art should understand that, after knowing the structure of the compound of the present application, the compound of the present application can be obtained by various methods well known in the art, by using known raw materials in the art, such as methods of chemical synthesis or extraction from organisms (e.g., microorganisms), these methods are all included in the present application. In addition, the procyanidin is also a commercial drug, so its finished product is easily available to those skilled in the art.

In the present application, the pharmaceutically acceptable salt of procyanidin is also included, which also retains the chemical activity of procyanidin. In the present application, a “pharmaceutically acceptable” ingredient is a substance suitable for use in humans and/or animals without undue adverse side effects (e.g., toxicity, irritation and allergic reactions), that is a substance with a reasonable benefit/risk ratio. The “pharmaceutically acceptable salt” can be an acid salt or basic salt of procyanidin.

“Pharmaceutically acceptable acid salt” refers to a salt that can maintain the biological activity and properties of the free base, and such salt will not have undesired biological activity or other changes. Such salt may be formed from an inorganic acid, for example, but not limited to, hydrochloric acid, hydrobromic acid, sulfuric acid, nitric acid, phosphoric acid, and the like. Such salt may also be formed from an organic acid, for example, but not limited to, acetic acid, dichloroacetic acid, adipic acid, alginic acid, ascorbic acid, aspartic acid, benzenesulfonic acid, benzoic acid, 4-acetamidobenzoic acid, camphoric acid, camphorsulfonic acid, capric acid, caproic acid, caprylic acid, carbonic acid, cinnamic acid, citric acid, cyclamic acid, dodecylsulfonic acid, 1,2-ethanedisulfonic acid, ethanesulfonic acid, isethionic acid , formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, 2-naphthalenesulfonic acid, 1-naphthol-2-carboxylic acid, niacin, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and similar acids.

“Pharmaceutically acceptable basic salt” refers to a salt that can maintain the biological activity and properties of the free acid, and such salt will not have undesired biological activity or other changes. Such salt is prepared by adding an inorganic or organic base to the free acid. The salt derived from an inorganic base includes, but is not limited to, sodium salt, potassium salt, lithium salt, ammonium salt, calcium salt, magnesium salt, iron salt, zinc salt, copper salt, manganese salt, aluminum salt and the like. Preferred inorganic salt is ammonium salt, sodium salt, potassium salt, calcium salt and magnesium salt. The salt derived from an organic base includes but is not limited to primary, secondary, and tertiary ammonium salts, substituted amines include naturally substituted amines, cyclic amines, and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, N-Benzyl-2-phenylethylamine, N,N'-dibenzylethylenediamine, ethylenediamine, glucosamine, methylglucosamine, theobromine, triethanolamine , tromethamine, purine, piperazine, piperidine, N-ethylpiperidine, polyamide resin and similar structures. Preferred organic bases are isopropylamine, diethylamine, ethanolamine, trimethylamine, dicyclohexylamine, choline and caffeine.

The compound disclosed in the present patent may exist as a hydrate, including monohydrate, dihydrate, hemihydrate, sesquihydrate, trihydrate, tetrahydrate, and similar structures. In the present application, procyanidin prodrug is also included, and "prodrug" refers to a compound that undergoes metabolism or chemical reaction in the body of a subject and converts into the desired procyanidin after being taken in an appropriate way.

Procyanidin

The inventors found that procyanidin (herein referred to as PCC1) can effectively inhibit the expression of SASP and significantly reduce the survival rate of senescent cells.

Therefore, the present application provides a use of procyanidin in the manufacture of a medicament or preparation, the medicament or the preparation is used for: downregulating senescence-associated secretory phenotype (SASP), reducing the expression or activity of SASP factors, reducing the expression or activity of cell senescence marker factors, inducing apoptosis of non-proliferating cells, reducing or eliminating non-proliferating cells, delaying senescence, prolonging lifespan in a subject, reducing age-related disease burden in a subject, preventing, alleviating and treating a disease that would benefit from the reduction or elimination of non-proliferating cells, reducing resistance to cancer therapy, promoting tumor regression, reducing tumor size, preventing or treating cancer, or prolonging cancer survival. Herein, "individual", "subject" or "patient" refers to a mammal, especially a human.

In this article, "elimination" and "clearance" are used interchangeably, indicating that the substance uses the cell's own mechanism to selectively destroy non-proliferating cells (senescent cells) to achieve the effect of cell death and clearance. In an exemplary embodiment, a substance (e.g., PCC1) can eliminate or clean non-proliferating cells by inducing apoptosis.

"SASP factors" as used herein include extracellular matrix proteins, inflammatory cytokines and cancer cell growth factors. The SASP factors may include the factors shown in FIG. 6 or one or more selected from: IL6, CXCL8, MCP2, CXCL1, GM-CSF, MMP3, AREG, SFRP2, ANGPTL4, IL1a.

The "disease benefiting from the reduction or elimination of non-proliferating cells" described herein are generally an age-related disease, including but not limited to cancer, cardiovascular and cerebrovascular disease, osteoporosis, age-related degenerative joint disease (e.g., arthritis), metabolic disease, neurodegenerative disease. Preferably, the cancer is a prostate cancer.

Herein, procyanidin (e.g., PCC1) can also be used to extend the lifespan of a subject and reduce age-related disease burden in a subject. In some embodiments, the subject is an elderly subject, for example, the subject corresponding to a mouse of at least 20 months of age or a human of at least 60 years of age. Preferably, the elderly subject is a subject corresponding to a mouse of at least 24 months of age or a human of at least 75 years of age. More preferably, the elderly subject is a subject corresponding to a mouse of 24-27 months of age or a human of 75-90 years of age. Although the elderly subject is used as a research subject in specific embodiments, this is only an example for the convenience of result analysis (for example, an older subject has more age-related diseases). Based on the efficacy of procyanidin in eliminating senescent cells found in the present application, those skilled in the art should know that it can be used in a subject of any age to eliminate senescent cells, prolong life, and reduce the burden of an age-related disease.

Herein, the procyanidin (e.g., PCC1) can also be used to reduce resistance to cancer therapy in a patient. The cancer therapy includes chemotherapy or radiation therapy; examples of chemotherapy include cytotoxic therapy such as MIT or DOX, and examples of radiation therapy include ionizing radiation, mainly including therapies with α-rays, β-rays, γ-rays and X-rays as well as proton and neutron flows.

Furthermore, the inventors found that when used in combination with a certain agent, the procyanidin (e.g., PCC1) can enhance the cytotoxicity of the agent for inducing cell senescence. The agent for inducing cell senescence may be an agent that induces to produce senescent cells by causing DNA damage and/or apoptosis, and examples thereof include chemotherapeutic agents or radiation.

Therefore, the present application also provides a use of the procyanidin in enhancing the efficacy of an agent that induces cell senescence, and a use of procyanidin in combination with an agent that induces cell senescence in promoting tumor regression, reducing tumor volume, preventing or treating cancer, and prolonging cancer survival. Exemplarily, the cell is a tumor cell; the tumor is a prostate tumor; and the cancer is a prostate cancer.

In another aspect of the present application, there is provided a method for achieving the above use, and the method comprises: using (a) the procyanidin described herein or pharmaceutically acceptable salt, hydrate or prodrug thereof, and optionally (b) an agent capable of inducing a senescent cell in a subject, to treat a senescent cell or administer them to a subject in need thereof. The term "administering" or "giving" as used herein refers to providing a compound or pharmaceutical composition of the present application to a subject suffering from a disease or condition to be treated or prevented or at risk of a disease or condition.

Composition

The composition of the present application uses a substance such as procyanidin or salt thereof as an active component. As mentioned above, the composition containing the procyanidin (e.g., PCC1) is capable of down-regulating senescence-associated secretory phenotype (SASP), reducing expression or activity of SASP factors, reducing expression or activity of cell senescence marker factors, inducing apoptosis of non-proliferating cells (senescent cells), reducing or eliminating non-proliferating cells (senescent cells), delaying aging, prolonging lifespan in a subject, reducing age-related disease burden in a subject, preventing, relieving and treating a diseases that would benefit from the reduction or elimination of non-proliferating cells, reducing resistance to cancer therapy.

When the composition further comprises a cell senescence-inducing agent (e.g., a chemotherapeutic agent or radiation) as an active component, the composition can promote tumor regression, reduce tumor volume, prevent or treat a cancer, and prolong cancer survival.

When the composition described herein is used as a medication, it also contains a pharmaceutically acceptable auxiliary material. "Pharmaceutically acceptable auxiliary material" is a pharmaceutically or food-acceptable carrier, solvent, suspending agent or excipient that can be used to deliver the active components in the composition of the present application (e.g., procyanidin and optional cell senescence-inducing agent) to an animal or human. Exemplary auxiliary material can be a liquid or solid, and includes, but is not limited to: pH adjuster, surfactant, carbohydrate, adjuvant, antioxidant, chelating agent, ionic strength enhancer, preservative, carrier, glidant, sweetener, dye/coloring agent, flavor enhancer, wetting agent, dispersant, suspending agent, stabilizer, isotonic agent, solvent, emulsifier, atomizing agent, compressed air or other suitable gases, or other suitable inactive ingredients used in combination with medicinal compounds. More specifically, suitable auxiliary material may be those commonly used in the art for the administration of small molecule compounds. Examples of auxiliary material include various lactose, mannitol, oils such as corn oil, buffers such as PBS, saline, polyethylene glycol, glycerol, polypropylene glycol, dimethylsulfoxide, amides such as dimethylacetamide, proteins such as white protein, and detergents such as Tween 80, monosaccharides and oligopolysaccharides such as glucose, lactose, cyclodextrin and starch.

In general, the composition will contain a therapeutically effective amount of the active ingredient described herein. A therapeutically effective amount refers to a dose that can achieve treatment, prevention, alleviation and/or relief of a disease or condition in a subject. The therapeutically effective amount can be determined according to factors such as the patient's age, sex, disease and its severity, and other physical conditions of the patient. A therapeutically effective amount may be administered as a single dose, or may be administered in multiple doses in accordance with an effective treatment regimen. Herein, a subject or a patient generally refers to a mammal, especially a human. Exemplarily, the composition comprises, for example, 0.001-50%, preferably 0.01-30%, more preferably 0.05-10% by weight of the active ingredients (e.g., the procyanidin and the optional cell senescence-inducing agent).

The pharmaceutical composition or mixture of the present application can be prepared into any conventional preparation form by conventional methods. Dosage forms can be diverse, the dosage form is acceptable as long as the active ingredients can effectively reach the body of the mammal. For example, it can be selected from: injection, infusion, tablet, capsule, pill. Wherein, the active components (e.g., the procyanidin and the optional cell senescence inducing reagent) can exist in a suitable solid or liquid carrier or diluent. The mixture of active ingredients or the pharmaceutical composition of the present application may also be stored in a sterile device suitable for injection or infusion.

The effective doses of the active ingredients in the composition (e.g., the procyanidin and the optional cell senescence-inducing agent) may vary with the administration mode and the severity of the disease to be treated, which can be based on the experience and recommendations of clinicians.

In a specific embodiment of the present application, there is provided a series of dosage regimens for the procyanidin and the optional cell senescence-inducing agent according to different molar ratios or mass ratios. In the present application, mice are also used as experimental animals. It is easy for those skilled in the art to convert the dosage for mice into the dosage suitable for humans. For example, it can be calculated according to the Meeh-Rubner formula:

$$A = k * (W^{2/3})/10000.$$

In the formula, A represents the body surface area, expressed in $m^2$; W represents the body weight, expressed in g; K represents a constant, which varies with animal species, that is, 9.1 for mouse and rat, 9.8 for guinea pig, 10.1 for rabbit, 9.9 for cat, 11.2 for dog, 11.8 for monkey, and 10.6 for human.

The procyanidin and the optional cell senescence-inducing agent or the pharmaceutical composition can be administered orally, intravenously, intramuscularly or subcutaneously, etc. Oral administration may be preferred. Pharmaceutical forms suitable for oral administration include, but are not limited to, tablet, powder, capsule, sustained-release formulation, and the like. The pharmaceutical forms suitable for injection include: sterile aqueous solution or dispersion and sterile powder. In all cases, these forms must be sterile and must be fluid to easily drain from syringe.

When necessary, the procyanidin and the optional cell senescence-inducing agent can also be administered in combination with an additional active ingredient or drug.

The present application also provides a medicine box or kit for down-regulating or clearing senescent cells, or prolonging lifespan of an organism, and the medicine box or the kit comprises the pharmaceutical composition described in any embodiment herein. Alternatively, the medicine box or the kit comprises a mixture of the procyanidin described herein and the optional cell senescence-inducing agent. Alternatively, the medicine box or the kit comprises: Container 1, and the procyanidin or the pharmaceutically acceptable salt, hydrate or prodrug thereof described herein placed in Container 1; and Container 2, and the cell senescence-inducing reagent placed in Container 2.

The medicine box or the kit may also comprise some auxiliary materials, such as measuring tool and container such as syringe and the like required for using or administering the composition in various dosage forms. The medicine box or the kit can also comprise instructions for use, explaining the method of treating, down-regulation or clearing senescent cells or prolonging the survival period of body.

EXEMPLARY EMBODIMENTS

1. A pharmaceutical composition, comprising (a) a procyanidin or a pharmaceutically acceptable salt, hydrate or prodrug thereof, and (b) an agent capable of inducing a subject to produce a senescent cell, and optionally a pharmaceutically acceptable auxiliary material, preferably, the procyanidin is an oligomeric procyanidin.

2. The pharmaceutical composition as described in item 1, wherein, the procyanidin or the pharmaceutically acceptable salt, hydrate or prodrug thereof has a final concentration of at least 1 μM in the pharmaceutical composition, and/or the procyanidin is procyanidin C1, and/or the agent comprises an agent capable of causing DNA damage and/or apoptosis.

3. Use of a procyanidin or a pharmaceutically acceptable salt, hydrate or prodrug thereof in the manufacture of a medicament or preparation, the medicament or the preparation is used for: down-regulating senescence-associated secretory phenotype (SASP), reducing expression or activity of a SASP factor, reducing expression or activity of a cell senescence marker factor, inducing apoptosis of a non-proliferating cell, reducing or eliminating a non-proliferating cell, delay aging, prolonging lifespan of a subject, reducing an age-related disease burden of a subject, preventing, alleviating and treating a disease benefiting from the reduction or elimination of a non-proliferating cell, reducing resistance to a cancer therapy, enhancing efficacy of an agent capable of inducing cell senescence, promoting tumor regression, reducing tumor size, preventing or treating a cancer, or prolonging cancer survival, preferably, the procyanidin is an oligomeric procyanidin.

4. The use as described in item 3, wherein, the procyanidin is procyanidin C1, and/or the SASP factor includes extracellular matrix protein, inflammatory cytokine and cancer cell growth factor, and/or the non-proliferating cell is a senescent cell, preferably a naturally senescent or damaged cell, and/or the diseases benefiting from the reduction or elimination of a non-proliferating cell is an age-related disease, preferably cancer, cardiovascular and cerebrovascular disease, osteoporosis, age-related degenerative joint disease, metabolic disease, neurodegenerative disease, and/or the agent capable of inducing cell senescence comprises an agent capable of causing DNA damage and/or apoptosis, and/or the subject is an elderly subject, and/or the cancer therapy comprises chemotherapy or radiation therapy.

5. The use as described in item 3 or 4, wherein the tumor is a prostate tumor and/or the cancer is a prostate cancer.

6. Use of a substance in the manufacture of a medicament or preparation, in which the substance comprises (a) a procyanidin or a pharmaceutically acceptable salt, hydrate or prodrug thereof, and (b) an agent capable of inducing a subject to produce a senescent cell, the medicament or preparation is used for: promoting tumor regression, reducing tumor size, preventing or treating a cancer, or prolonging cancer survival, preferably, the procyanidin is an oligomeric procyanidin, more preferably procyanidin Cl, preferably, the agent capable of inducing a subject to produce a senescent cell comprises an agent capable of causing DNA damage and/or cell apoptosis.

7. The use as described in item 6, wherein the tumor is a prostate tumor and/or the cancer is a prostate cancer.

8. A medicine box or kit comprising the pharmaceutical composition as described in item 1 or 2, preferably, the medicine box or kit comprises Container 1 and Container 2, which respectively contain (a) the procyanidin or the pharmaceutically acceptable salt, hydrate or prodrug thereof and an optional pharmaceutically acceptable auxiliary material, and (b) the agent capable of inducing a subject to produce a senescent cell, and an optional pharmaceutically acceptable auxiliary material, preferably, the procyanidin is an oligomeric procyanidin, more preferably procyanidin Cl.

9. A method for changing a non-proliferating cell, in which the method comprises treating the non-proliferating cell with a procyanidin or a pharmaceutically acceptable salt, hydrate or prodrug thereof, and the changing comprises one or more selected from the following: down-regulating senescence-associated secretory phenotype (SASP), reducing expression or activity of a SASP factor, reducing expression or activity of a cell senescence marker factor, inducing apoptosis of a non-proliferating cell, reducing or eliminating a non-proliferating cell, or reducing resistance of a cell to a cancer therapeutic treatment, preferably, the procyanidin is an oligomeric procyanidin, more preferably procyanidin Cl, and/or the procyanidin or the pharmaceutically acceptable salt, hydrate or prodrug thereof has a final concentration of at least 1 μM.

10. A method for enhancing cytotoxicity of an agent capable of inducing cell senescence, in which the method comprises: using (a) a procyanidin or pharmaceutically acceptable salt, hydrate or prodrug thereof, and (b) an agent capable of inducing cell senescence, to treat a cell, preferably, the procyanidin is an oligomeric procyanidin, more preferably procyanidin Cl, and/or the agent capable of inducing cell senescence is capable of causing DNA damage and/or apoptosis, and/or the procyanidin or the pharmaceutically acceptable salt, hydrate or prodrug thereof has final concentration of at least 10 μM.

Unless defined otherwise, all technical and scientific terms used herein have the same meaning as commonly understood by one of ordinary skill in the art to which this application belongs. Although any methods and materials similar or equivalent to those described herein can be used in the practice or testing of the present application, the preferred methods and materials are now described. All publications and patents specifically mentioned herein are hereby incorporated by reference in their entirety for all purposes including describing and disclosing the chemicals, devices, statistical analyzes and methodologies reported in the publications which could be used in connection with the present application. All references cited in this description should be considered as indicative of the state of the art. Nothing herein is to be construed as an admission that the present application is not entitled to antedate such disclosure by virtue of any prior application.

The present application is further illustrated below in conjunction with specific examples. It should be understood that these examples are only used to illustrate the present application and are not intended to limit the scope of the present application. The experimental methods not indicating specific conditions in the following examples are usually according to conventional conditions such as those described in J. Sambrook et al., Molecular Cloning Experiment Guide, the third edition, Science Press, 2002, or according to the conditions recommended by the manufacturers.

EXAMPLES

Materials and methods

1. Cell Culture

(1) Cell Line Maintenance

The primary normal human prostate stromal cell line PSC27 (obtained from Fred Hutchinson Cancer Research Center, USA) was cultured in an incubator at 37° C. and 5% $CO_2$, and proliferated and passaged in PSCC complete culture medium.

(2) Cell Cryopreservation and Recovery a. Cell Cryopreservation

Cells in the logarithmic growth phase were collected with 0.25% trypsin, centrifuged at 1000 rpm for 2 min, the supernatant was discarded, and the cells were resuspended in freshly prepared freezing solution. The cells were subpackaged into labeled sterile cryovials. Then they were cooled by reducing temperature in gradient manner, and finally transferred to liquid nitrogen for long-term storage.

b. Cell Recovery

The cells frozen in liquid nitrogen were taken out and immediately placed in a 37° C. water bath to allow them to thaw quickly. 2 mL of cell culture medium was added directly to suspend the cells evenly. After the cells adhered to the wall, fresh culture medium was used for replacement.

(3) In Vitro Experimental Treatment

To cause cell damage, 50 μg/mL bleomycin (BLEO) was added to the culture medium when PSC27 cells grew to 80% (abbreviated as PSC27-CTRL). After 12 hours of drug treatment, the cells were simply washed 3 times with PBS, left in the culture medium for 7-10 days, and then the subsequent experiments were performed.

2. Screening of Natural Product Libraries

Pharmacodynamic analysis was conducted on a natural product library (BY-HEALTH) with a total of 41 components, most of which were medicinal plant extracts and had anti-senescence potential. Each product was diluted to a 96-well plate according to a certain concentration gradient, and the density was 5000 cells per well. The medium uses DMEM, and the working concentration of natural product (or compound) is generally controlled at 1 μM to 1 mM. After 3-7 days of drug treatment, cell proliferation was measured with CCK-8 Cell Counting Kit (based on WST-8 principle, Vazyme), and cell apoptosis activity was determined with Caspase 3/7 Activity Kit (Promega).

The initially identified drug candidates were further screened for 30 days. Drugs entering the second-round candidate range were diluted into a 6-well plate at 20,000 cells per well. Medium and drug candidates were changed every other day. In order to determine the effect of each drug on cell phenotype and viability, etc., the confirmatory analysis was performed according to different concentrations of drugs.

3. Western Blotting and Immunofluorescence Detection

Cell lysate-derived proteins were separated using NuPAGE 4-12% Bis-Tris gel and transferred to nitrocellulose membranes (Life Technologies). The blot was blocked with 5% skimmed milk for 1 h at room temperature, incubated overnight at 4° C. with the desired primary antibody at the manufacturer's protocol concentration, and then incubated with horseradish peroxidase-conjugated secondary antibody (Santa Cruz) for 1 h, blot signal detection was carried out with enhanced chemiluminescence (ECL) detection reagent (Millipore) according to the manufacturer's protocol, and ImageQuant LAS 400 Phospho-Imager (GE Healthcare) was used. As a standard protein marker, we used PageRuler Plus Prestained Protein Ladder (no. 26619) from Thermo Fisher Scientific.

For immunofluorescent staining, target cells were pre-seeded on coverslips for at least 24 h after culture in dishes. After a brief wash, the cells were fixed with 4% paraformaldehyde in PBS for 8 min and blocked with 5% normal goat serum (NGS, Thermo Fisher) for 30 min. Mouse monoclonal antibody-anti-phospho-Histone H2A.X (Ser139) (clone JBW301, Millipore) and mouse monoclonal antibody-anti-BrdU (Cat# 347580, BD Biosciences), and secondary antibody Alexa Fluor® 488 (or 594)-Eurolink's F(ab')2 were sequentially added to the slides coated with the fixed cells. Nuclei were counterstained with 2 μg/m DAPI. The most representative image was selected from the three observation fields for data analysis and result display. FV1000 laser scanning confocal microscope (Olympus) was used to acquire confocal fluorescence images of cells.

4. Whole-transcriptome Sequencing Analysis (RNA-sequencing)

Whole-transcriptome sequencing was performed on the primary human prostate stromal cell line PSC27 under different treatment conditions. Total RNA samples were obtained from stromal cells. Their integrity was verified by Bioanalyzer 2100 (Agilent), RNA was sequenced by Illumina HiSeq X10, and gene expression levels were quantified by software package rsem (https://deweylab.github.io/rsem/). Briefly, rRNA was depleted from RNA samples with the RiboMinus Eukaryote Kit (Qiagen, Valencia, Calif., USA); and according to the manufacturer's instructions, TruSeq Stranded Total RNA Preparation Kits (Illumina, San Diego, Calif.), USA) was used to construct a strand-specific RNA-seq library before deep sequencing.

Paired-end transcriptomic reads were mapped to a reference genome (GRCh38/hg38), and reference-annotation was performed from Gencode v27 using the Bowtie tool. Duplicate reads were identified using the picard Tools (1.98) script to mark duplicates (https://github.com/broadinstitute/picard), and only non-duplicate reads were retained. Reference splice junctions were provided by reference transcriptome (Ensembl Build 73). FPKM values were calculated with Cufflinks, and Cufflinks maximum likelihood estimation function was used to call differential gene expression. Genes with significant changes in expression were defined by false discovery rate (FDR)-corrected P-values<0.05, and only Ensembl Genes 73 with status "Known" and biotype "coding" were used for downstream analysis.

Next, Trim Galore (v0.3.0) (http://www.bioinformatics.babraham.ac.uk/projects/trim_galore/) was used to trim the reads, while the quality assessment was carried out by using FastQC (v0.10.0) (http://www.bioinformatics.bbsrc.ac.uk/projects/fastqc/). Subsequently, a preliminary analysis of the raw data was perform on a free online platform, Majorbio I-Sanger Cloud Platform (www.i-sanger.com), by using DAVID bioinformatics platform (https://david.ncifcrf.gov/) and Ingenuity Pathways Analysis (IPA) program (http://www.ingenuity.com/index.html), the raw data were deposited in the NCBI Gene Expression Omnibus (GEO) database with access code GSE156448.

5. Protein-protein Interaction Network Analysis

Protein-protein interaction (PPI) analysis was performed with STRING3.0. Specific proteins that met the criteria were imported into the online analysis software (http://www.networkanalyst.ca), and further hub and module analysis was performed by selecting a minimal interaction network.

6. Gene Set Enrichment Analysis (GSEA)

Based on the data obtained from the preliminary analysis of RNA-seq, analyzed and compared each differentially expressed significant gene, the genes were sorted using the "wald statistics" obtained from DESeq2, GSEA was performed on the sorting lists of all planning gene sets available in MSigDB (http://software.broadinstitute.org/gsea/msigdb). DESeq2 independent filtering was based on the average of normalized read counts to select genes with very low expression levels. The GSEA signature of SASP was as described in our previous publication (Zhang et al., 2018a).

7. Measurement of Gene Expression By Quantitative PCR (RT-PCR)

(1) Extraction of Total Cellular RNA

Total RNA of cells in the growth phase or stasis phase was extracted with Trizol reagent, 1 mL Trizol was added to each T25 culture flask, the cell layer was scraped off with a cell scraper, transferred into a centrifuge tube, and mixed well until not viscous. 0.2 mL of chloroform was added for every 1 mL of Trizol, shaken vigorously for 15 seconds, incubated at room temperature for 5-10 minutes; centrifuged at 11,000 g for 15 minutes at 4° C.; the colorless supernatant was transferred into a new centrifuge tube, added with 0.5 mL of isopropyl alcohol per 1 mL Trizol, incubated at room temperature for 10 minutes, centrifuged at 11,000 g and 4° C. for 10 minutes; the supernatant was discarded, washing was performed with 75% ethanol (at least 1 mL 75% ethanol per 1 mL Trizol was used), centrifuged at 4° C. and 7,500 g for 5 minutes; the RNA pellet was dried at room temperature for 5-10 minutes (RNA could not be dried), and the pellet was dissolved with DEPC-$H_2O$. After the RNA was quantified by a spectrophotometer, a small amount of total RNA was taken for 1% agarose electrophoresis to check the status and quality of the RNA.

(2) Reverse Transcription Reaction

Oligo-$dT_{23}$ $V_N$ (50 μM), 1 ul; total RNA, 1-2 ug; RNase-free $ddH_2O$ was added to 8 ul, heated at 65° C. for 5 minutes, quickly placed on ice to quench, and allowed to stand for 2 minutes.

Preparation of first-strand cDNA synthesis solution: 2×RT Mix, 10 ul; HiScript II Enzyme Mix, 2 ul. The first-strand cDNA synthesis was carried out according to the following conditions: 5 minutes at 25° C., 45 minutes at 50° C., and 5 minutes at 85° C.

(3) Real-time Quantitative PCR Reaction

The reverse transcription reaction product cDNA was diluted 50 times as a template. PCR reaction solution was prepared as follows: AceQ SYBR Green Master Mix, 10 ul; primer 1 (10 μM), 0.4 ul; primer 2 (10 uM), 0.4 ul; Rox Reference Dye, 0.4 ul; template, 2 ul; added with $ddH_2O$ to 20 ul.

Sample was loaded according to the above standard, and the reaction conditions were: 95° C. pre-denaturation for 15 seconds, then 95° C. for 5 seconds, 60° C. for 31 seconds, 40 cycles; melting curve conditions were 95° C. for 15 seconds, 60° C. for 30 seconds, 95° C. for 15 seconds. The sample was reacted on ABI ViiA7 (ABI) instrument. The expression of (3-actin was used as an internal reference. After the reaction was completed, the amplification of each gene was checked by software analysis, the corresponding threshold cycle number was derived, and the relative expression of each gene was calculated using the 2-AACt method. The peak and waveform of the melting curve was analyzed to determine whether the obtained amplification product was a specific single target fragment.

Wherein, the detection primer sequences used were as follows, F represented the forward primer, and R represented the reverse primer:

IL6 (F: SEQ ID NO:1, R: SEQ ID NO:2); CXCL8 (F: SEQ ID NO:3, R: SEQ ID NO:4); SPINK1 (F: SEQ ID NO:5, R: SEQ ID NO:6); WNT16B (F: SEQ ID NO:7, R: SEQ ID NO:8); GM-CSF (F: SEQ ID NO:9, R: SEQ ID NO:10); MMP3 (F : SEQ ID NO: 11, R: SEQ ID NO: 12); IL-1α (F: SEQ ID NO: 13, R: SEQ ID NO: 14); p 16INK4a (F: SEQ ID NO: 15, R: SEQ ID NO: 16); IL-1(3 (F: SEQ ID NO: 17, R: SEQ ID NO: 18); AREG (F: SEQ ID NO:19, R: SEQ ID NO:20); CXCL1 (F: SEQ ID NO:21, R: SEQ ID NO:22); CXCL3 (F: SEQ ID NO:23, R: SEQ ID NO:24); p21CIP1 (F: SEQ ID NO:25, R: SEQ ID NO:26); BMP6 (F: SEQ ID NO:27, R: SEQ ID NO:28).

8. SA-β-Gal Staining

Senescence-associated (3-galactosidase (SA-β-Gal) staining was performed following a previously reported procedure (Debacq-Chainiaux et al., 2009). Briefly, cells in culture dishes were washed with PBS and fixed at room temperature. Cells were fixed in 2% formaldehyde and 0.2% glutaraldehyde for 3 minutes. SA-β-Gal was used for staining with freshly prepared staining solution overnight at 37° C. Images were taken on the next day and the percentage of positive cells per unit area was calculated.

9. Clonal Expansion Experiment

Single-cell clonal expansion experiment was performed as previously described (Duan et al., 2015; Wu et al., 2018). Briefly, cells were plated in gelatin-coated 12-well plates at a density of 2000 cells/well. Cell clones were counted after crystal violet staining.

10. Drug-induced Apoptosis in Senescent Cells

PSC27 cells were plated in a 96-well dish, and the cells were induced to senescence under the treatment of 50 μg/mL BLEO. PCC1 and ABT263 were added at concentrations of 50 μM and 1.0 μM, respectively. Cell culture medium was supplemented with Incucyte Nuclight fast Red Reagent (Essen Bioscience) and Incucyte C-3/7 Apoptosis Reagent (Essen Bioscience). Representative field of view was selected to take pictures.

11. Mouse Xenograft Inoculation and Preclinical Treatment Trials

All experimental mouse experiments were carried out in strict accordance with the relevant regulations of the Institutional Animal Care and Use Committee (IACUC), Shanghai Institutes for Biological Sciences, Chinese Academy of Sciences. Immunodeficient mice (NOD-SCID mice, ICR) (body weight about 25 g) aged 6-8 weeks were used for animal experiments related to the present patent. Stromal cells PSC27 and epithelial cells PC3 were mixed at a predetermined ratio of 1:4, and each graft contained 1.25×10 6 cells for tissue remodeling. The xenograft tumors were implanted into mice by subcutaneous transplantation, and the animals were euthanized 8 weeks after the end of the transplantation surgery. Tumor volume was calculated according to the following formula: $V=(\pi/6)\times((1+w)/2)^3$ (V, volume; l, length; w, width).

In a preclinical treatment trial, subcutaneously transplanted mice were fed with a standard experimental diet, after 2 weeks chemotherapy drugs mitoxantrone (MIT, dose: 0.2 mg/kg) and/or procyanidin C1 (PCC1) (500 μl, dose: 10 mg/kg) via intraperitoneal administration. The time points were: the former was administrated on the first day of the $3^{rd}$, $5^{th}$ and $7^{th}$ weeks, and the latter was administrated on the first day of the $5^{th}$ and $7^{th}$ weeks. A total of 3 cycles of MIT administration were carried out throughout the course of treatment, and each cycle lasted for 2 weeks. After the course of treatment, mouse tumors were harvested for volume measurement and histological analysis. Each mouse cumulatively received 0.6 mg/kg body weight of MIT and 30 mg/kg body weight of PCC1. In order to cause systemic expression of SASP factor induced by chemotherapy, MIT was administered to mice through intravenous infusion according to the above steps and sequence, but the dose was reduced to 0.1 mg/kg body weight/each time (the cumulative dose of MIT received in the whole course of treatment was 0.3 mg/kg body weight) to reduce drug-related toxicity. The chemotherapy experiment ended at the end of the $8^{th}$ week, and the mice were dissected immediately after sacrifice, and the xenograft tumors were collected and used for pathological system analysis.

12. Study on Mouse Lifespan

For the cell transplantation study, we obtained 16-month-old male C57BL/6 mice by serial rearing in the SPF animal platform, with 4 to 5 animals per cage. We first sorted the mice by body weight from low to high, and then selected mice with similar body weights. Next, the mice were assigned to senescence (SEN) or control (CTRL) transplant treatment at each interval using a random number generator, while the middle mice were assigned to the other treatment, so that the body weights of the senescence and control transplant mice were matched. One month after cell transplantation, when the mice were 18 months old, physical function tests were performed. After that, no further testing was done on the mice other than checking their cages. The earliest deaths occurred approximately 2 months after the last physical function test. C57BL/6 mice aged 19 to 21 months were housed at 3-5 animals per cage. As with the transplanted mice, the mice were sorted by body weight and randomly assigned to each group, and treated in either control (vehicle) or drug (PCC1) group by persons blinded to the design of the preclinical trial. From the age of 24-27 months, the mice were treated with vehicle or PCC1 every 2 weeks, orally gavaged for 3 consecutive days at each time. During the course of the study, some mice were removed from their original cages in order to minimize the animal housing stress caused by long-term housing in a single cage. RotaRod and hanging tests were performed monthly because these tests were sensitive and noninvasive. At the end of the experiment, we euthanized the mice; we considered them dead if they exhibited one of the following symptoms: (i) unable to drink or eat; (ii) unwilling to move even when stimulated; (iii) rapid weight loss; (iv) severe balance disorder; or (v) body bleeding or ulcerated tumors. During the experiment, no mice were excluded due to fighting, accidental death or dermatitis. For biostatistics, we used a Cox proportional hazard model for survival analysis.

13. Post-mortem Pathological Examination of Preclinical Animals

The researchers checked the cages daily and removed dead mice from the cages. Within 24 hours of animal death, cadavers (abdominal cavity, thoracic cavity, and skull) were opened and kept separately in 10% formalin for at least 7 days. Decomposed or destroyed bodies were excluded. The preserved cadavers were transported to the dedicated autopsy site for pathological examination. Tumor burden (sum of different types of tumors per mouse), disease burden (sum of different histopathological changes in major organs per mouse), severity of each lesion and inflammation (lymphocyte infiltration) were assessed.

14. Bioluminescent Imaging

The mice were injected intraperitoneally with 3 mg of fluorescein (BioVision, Milpitas, Calif.), delivered in a volume of 200 μl in PBS. The mice were anesthetized with isoflurane, and bioluminescent images were acquired using a Xenogen IVIS 200 System (Caliper Life Sciences, Hopkinton, Mass.).

15. Physical Ability Test

All testing began on day 5 after the last placebo or drug treatment. Maximum walking speed was assessed using the accelerated RotaRod System (TSE System, Chesterfiled, Mo.). The mice were trained on the RotaRod for 3 days at speeds of 4, 6 and 8 r.p.m, lasted for 200 seconds on the $1^{st}$, $2^{nd}$ and $3^{rd}$ days. On the test day, the mice were placed on the RotaRod, and the test was performed starting at a speed of 4 r.p.m. The rotation speed was accelerated from 4 to 40 r.p.m at intervals of 5 minutes. When the mice fell off the RotaRod, the speed was recorded. The final results were averaged from 3 or 4 trials and normalized to baseline speed. The mice that had been trained within the previous two months were no longer trained.

Forelimb grip strength (N) was measured using a Grip Strength Meter (Columbus Instruments, Columbus, Ohio), and the results were averaged from more than 10 trials. For the hanging endurance test, the mice were placed on a 2 mm thick metal wire, while the later was 35 cm above a mat. The mice were only allowed to grasp the wire with their forelimbs, and the hang time was normalized to body weight and expressed as hang duration (sec) x body weight (g). The results were the average of 2 to 3 trials per mouse. Their daily activity and food intake were monitored for 24 h (12 hours of light and 12 hours of dark) by a Comprehensive Laboratory Animal Monitoring System (CLAMS). The CLAMS system was equipped with an Oxymax Open Circuit calorimeter System (Columbus Instruments). For treadmill performance, the mice were acclimatized to run on an electric running machine (Columbus Instruments) at a 5° incline, for 3 days of training, lasted for 5 minutes each day, started at a speed of 5 m/min for 2 minutes, then accelerated to 7 m/min for 2 minutes, then 9 m/min for 1 minute. On the day of the test, the mice ran on the treadmill at an initial speed of 5 m/min for 2 min, and then the speed increased by 2 m/min every 2 min until the mice were exhausted. Fatigue was defined as the inability of mice to return to the treadmill despite mild electrical and mechanical stimulation. The distance was recorded after the test, and the total work (KJ) was calculated with the following formula: mass (kg)×g (9.8 $m/s^2$)×distance (m)×sin) (5°).

16. Biostatistical Methods

In the present patent application, all in vitro experiments involving cell proliferation rate, survival rate and SA-β-Gal staining, and in vivo experiments on mouse xenograft tumors and preclinical drug treatment were repeated more than 3 times, and the data were presented in the form of mean±standard error. The statistical analyzes were established on the basis of raw data and calculated by one-way analysis of variance (ANOVA) or a two-tailed Student's t-test, while the results with $P<0.05$ were considered to be significantly different.

The correlation between factors was tested by Pearson's correlation coefficients. Cox proportional hazards model was used for survival analysis when mice were obtained in several cohorts and grouped in cages. In the model, sex and age were used in the treatment as fixed effects, while cohort and initial cage assignment were used as random effects. Since during the study some mice were moved from their initial cages to minimize stress from the single cage enclosure, we also performed analysis without cage effects. The results of the two analyzes did not differ significantly in directionality or statistical significance, which increased confidence in our results. Survival analysis was performed using the statistical software R (version 3.4.1; library 'coxme'). In most experiments and outcome assessments, investigators made blind selections for assignments. We used baseline body weights to assign mice to experimental groups (to achieve similar body weights between groups), so randomization was only performed within groups matched for body weight. We determined the sample size based on previous experiments and therefore did not use statistical power analysis. All replicates in this study were derived from different samples, and each sample was derived from a different experimental animal.

Figure 2:
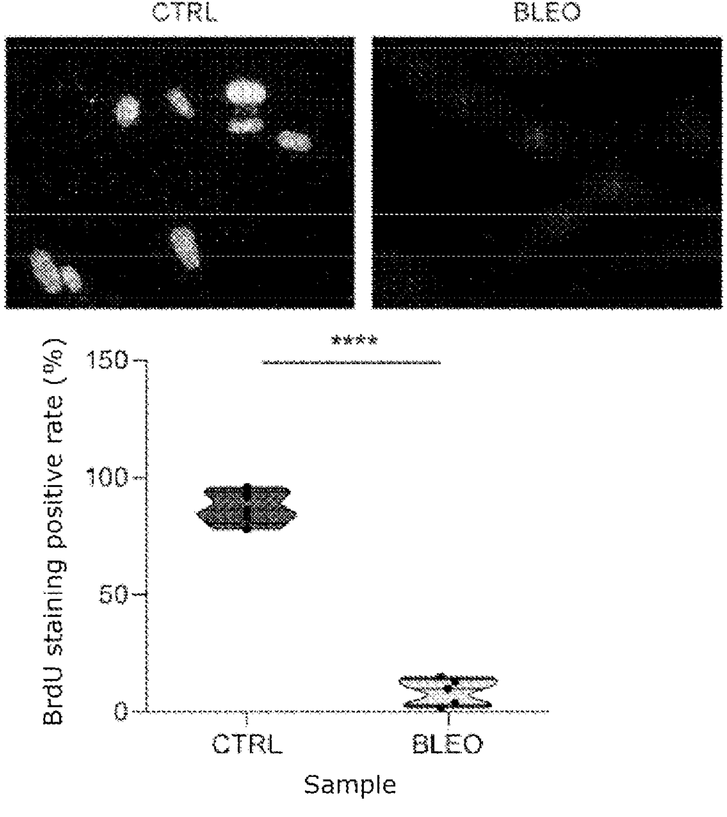
FIG. 2 shows the results of BrdU staining of PSC27 cells treated with chemotherapeutic drug bleomycin (BLEO), in which the upper part shows representative images, and lower part shows statistical data. CTRL, control cells; BLEO, cells treated with bleomycin. ***, P<0.001.
Figure 3:
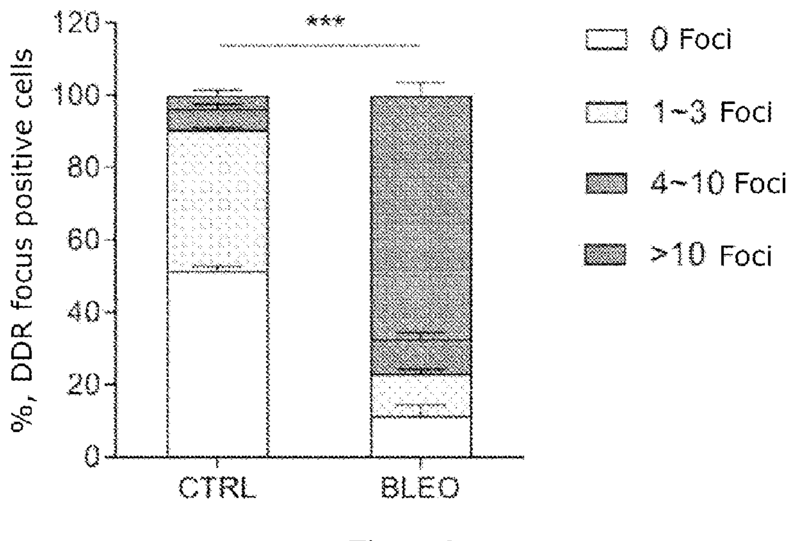
FIG. 3 shows the results of immunofluorescence staining using γH2AX after PSC27 cells were treated with chemotherapeutic drug bleomycin (BLEO). CTRL, control cells; BLEO, cells treated with bleomycin. ***, P<0.001. According to the number of fluorescent spots in the nucleus, they were divided into 4 categories, including single cells with 0 foci, 1 to 3 foci, 4 to 10 foci, and >10 foci.
Figure 4:
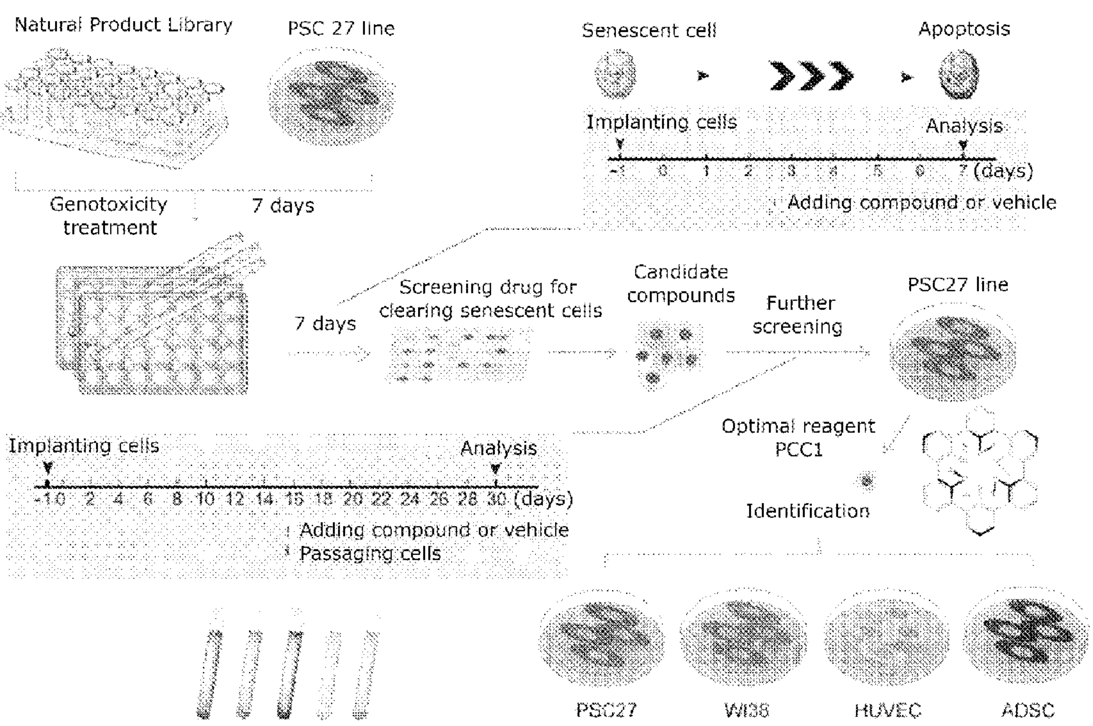
FIG. 4 shows an experimental flow chart for screening natural product drug libraries to obtain a plant raw material with anti-senescence activity.

Example 1: PCC1 Can Effectively Inhibit SASP Expression When Used at Low Concentration To identify innovative compounds capable of potently modulating phenotype of senescent cells, we performed an unbiased screen using a phytochemical library of 41 plant derivatives. In order to test the efficacy and potential biological value of these drugs, we chose to use the primary normal human prostate stromal cell line, PSC27, as an in vitro cell model. PSC27 is composed predominantly of fibroblasts, with non-fibroblastic cell lines (including endothelial cells and smooth muscle cells) also present, but in smaller proportions; and PSC27 is a human primary stromal cell line in nature, which forms typical SASP after exposure to stress factors such as genotoxic chemotherapy or ionizing radiation. We treated these cells with a specific dose of bleomycin (BLEO), which had been optimized in the preliminary experiment, and observed a significant increase in the positive rate of senescence-associated β-galactosidase (SA-β-Gal) staining, the BrdU incorporation rate was greatly reduced, and the DNA damage repair foci (DDR foci) were significantly increased within days after drug injury (FIG. 1 to FIG. 3). We performed a systematic screening to compare the effects of these natural drug products on the expression profiles of senescent cells in parallel mode (FIG. 4).

Figure 5:
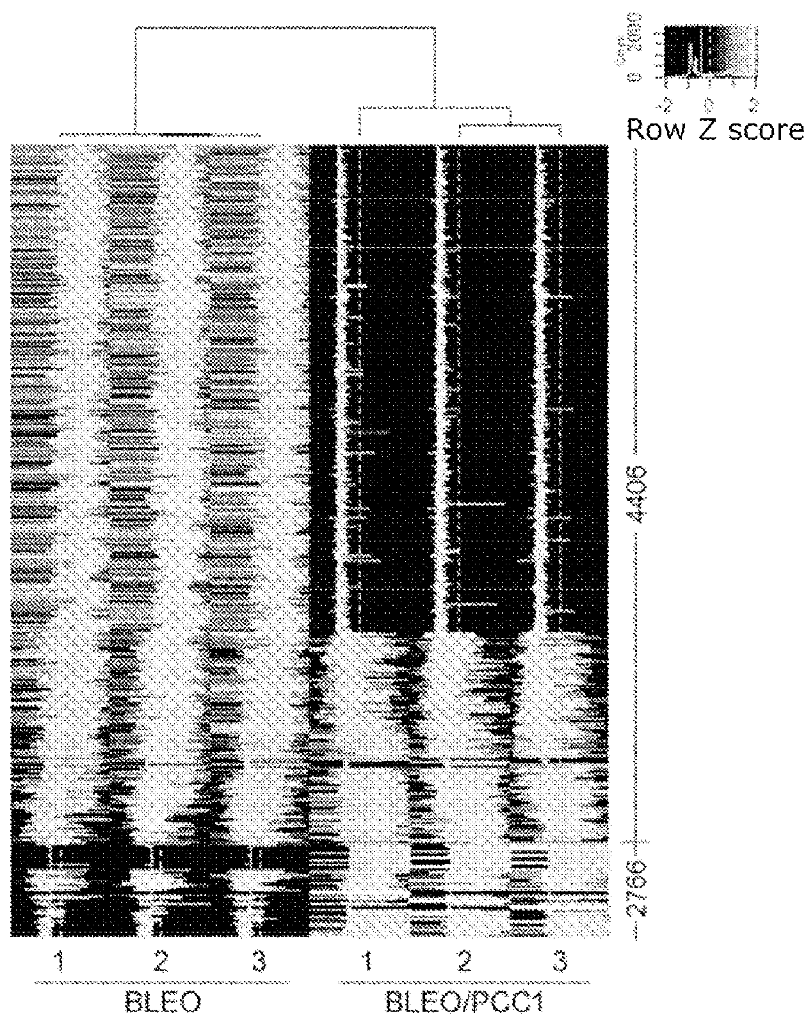
FIG. 5 shows that after the RNA-seq data is processed by software and bioinformatics analysis, it is found that PCC1 can significantly reduce the genes that are significantly upregulated in senescent cells compared with proliferating cells. Compared with the BLEO group, 4406 genes are significantly downregulated and 2766 genes are significantly upregulated in the BLEO/PCC1 group (fold change>2, P<0.01).
Figure 6:
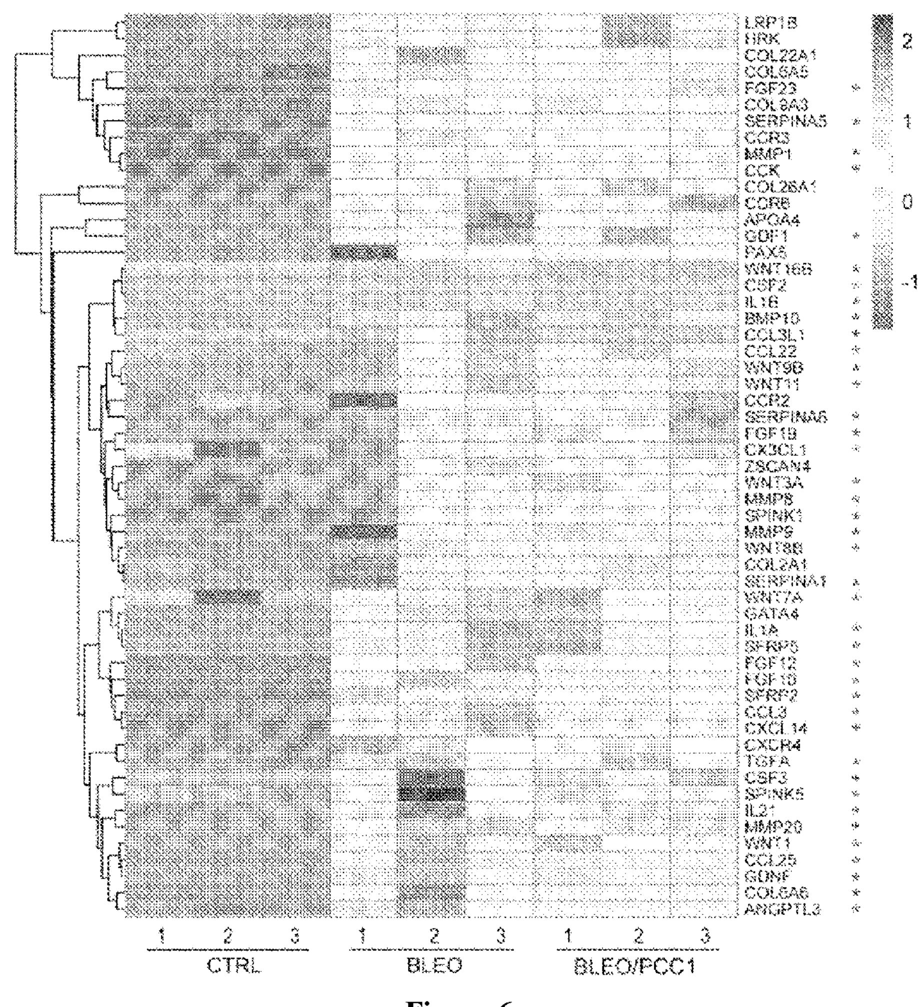
FIG. 6 shows that in the heatmap, the expression of a large number of factors in senescent cells caused by BLEO damage is upregulated, but many of them are significantly reversed after PCC1 treatment. Red star mark, typical SASP exocrine factor.
Figure 7:
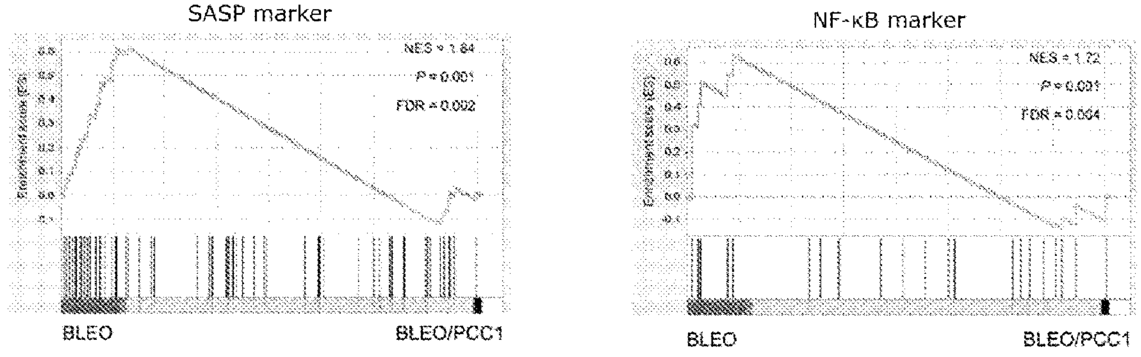
FIG. 7 shows that in the results of GSEA analysis, the expression of SASP or NF-κB molecular marker-related factors is intensively upregulated in BLEO-induced senescent cells, but significantly decreased after PCC1 treatment of senescent cells. Left, SASP molecular marker; right, NF-κB molecular marker.
Figure 8:
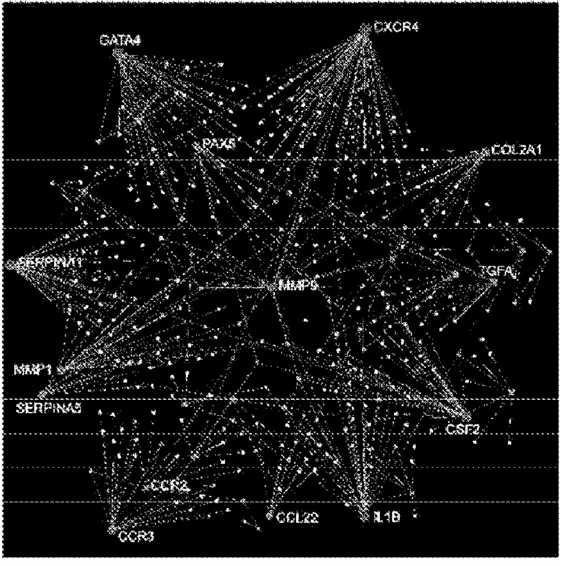
FIG. 8 shows that in the results of protein-protein interaction (PPI) bioinformatics analysis, PCC1 significantly downregulated senescent cell molecules form a network, and there are multiple interactions among them.
Figure 9:
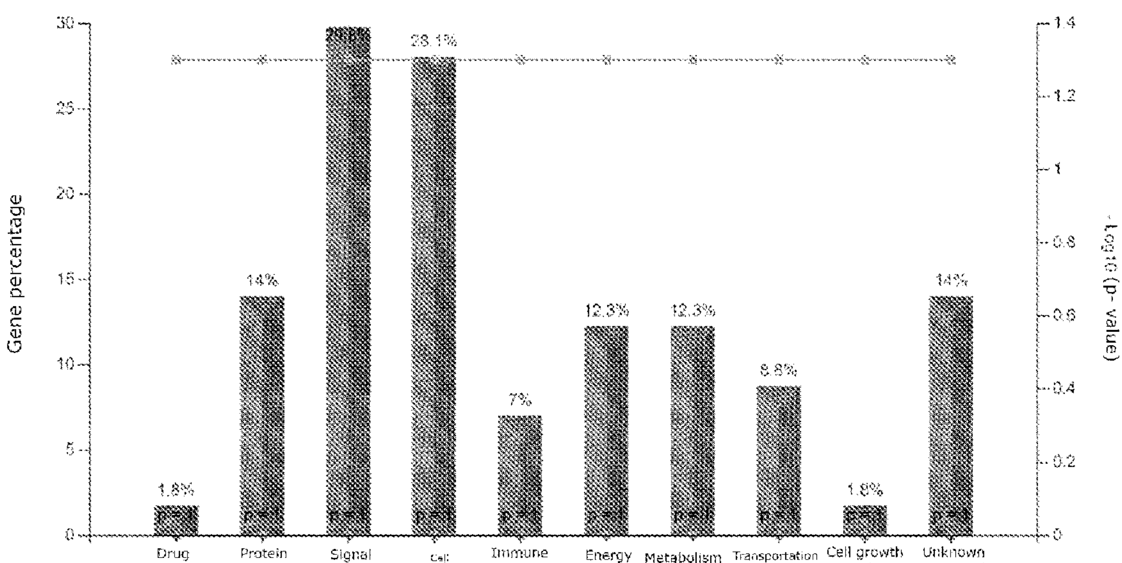
FIG. 9 shows the representative pathways of biological process for 100 molecules with significant downregulation caused by PCC1 in senescent cells according to the KEGG pathway analysis. Left Y axis, percentage. Right Y axis, log10(p-value).
Figure 10:
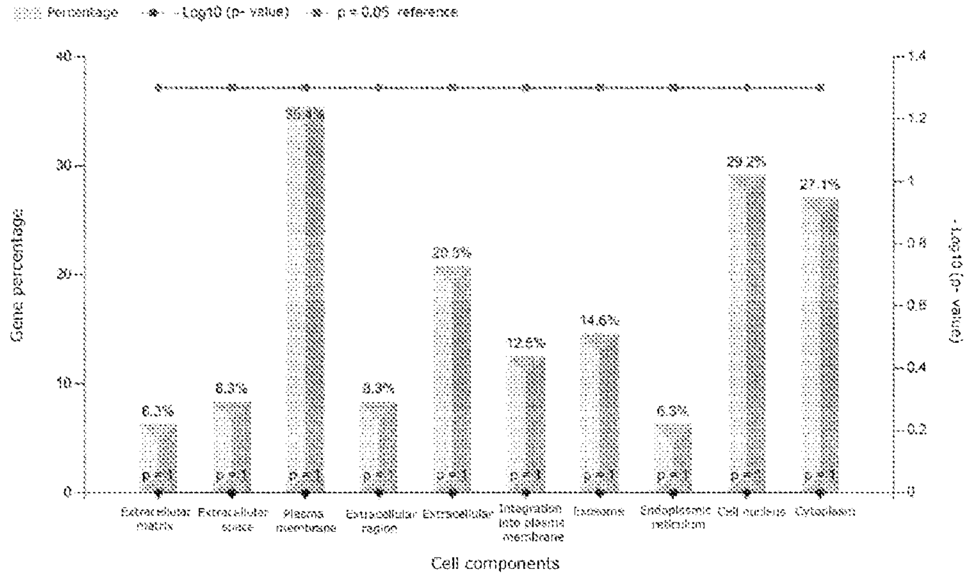
FIG. 10 shows the representative pathways of cellular component for 100 molecules with significant downregulation caused by PCC1 in senescent cells according to KEGG pathway analysis. Left Y axis, percentage. Right Y axis, log10(p-value).

We performed RNA-seq on these cells. Subsequently, the high-throughput data obtained showed that a plant raw material, procyanidin C1 (PCC1), significantly altered the expression profile of senescent cells. Among them, 4406 genes were significantly down-regulated, while 2766 genes were up-regulated, where the fold change of each gene in the heatmap was 2.0 ($P<0.01$) (FIG. 5). Importantly, the expression of SASP factors was generally decreased in senescent cells after PCC1 treatment, whereas these SASP factors were generally significantly up-regulated in senescent cells (FIG. 6). Although the expression profiles of some SASP-unrelated genes showed similar trends to those of typical SASP factors, the data from the GSEA analysis further revealed significant repression of molecular signatures characterizing SASP expression or NF-κB activation, which were major transcriptional event mediating the development of proinflammatory SASP (FIG. 7). The results of bioinformatics analysis based on protein-protein interactions revealed a highly active network involving multiple factors that were significantly up-regulated during cell senescence, but down-regulated once the cells were under the action of PCC1 (FIG. 8). Further GO bioinformatics data revealed that these molecules are functionally involved in a set of important biological processes, including signal transduction, intercellular communication, energy regulation, cellular metabolism, and inflammatory response (FIG. 9). Most of these down-regulated genes were biological proteins in nature that were released into the extracellular space after expression, or were located on the endoplasmic reticulum or Golgi apparatus, and generally corresponded characteristically to the secretory properties of these molecules (FIG. 10).

Figure 11:
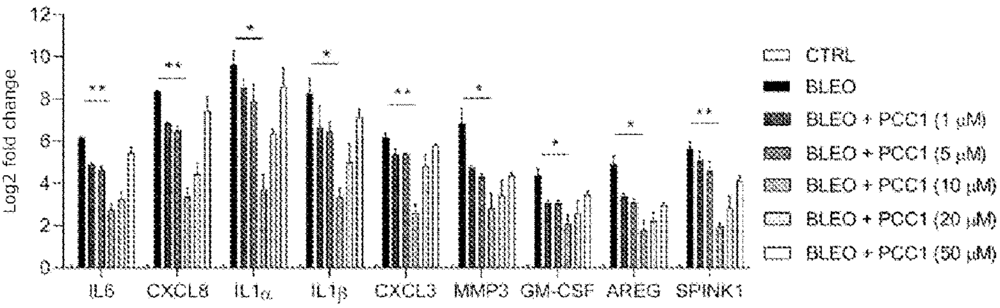
FIG. 11 shows the relative expression levels of a group of typical SASP molecules in senescent cells induced by BLEO and treated with different concentrations of PCC1 according to the detection and analysis of fluorescent quantitative PCR (qRT-PCR). All data are normalized results compared to the CTRL group. *, P<0.05; **, P<0.01.

To further confirm the effect of PCC1 on SASP expression under in vitro conditions, we treated PSC27 cells under a series of in vitro concentration gradients. The data showed that PCC1 at a working concentration of 10 μM inhibited SASP development with the greatest efficiency (FIG. 11). However, lower or higher concentrations of the drug were less effective, although the latter could be related to the cellular stress response caused by the drug's increased cytotoxicity (FIG. 11). Therefore, PCC1, a plant-based natural product, could be used to control the pro-inflammatory phenotype of senescent cells, namely SASP, especially at relatively low concentrations.

Example 2: PCC1 as Novel Senolytic Agent When Used at High Concentrations

Figure 12:
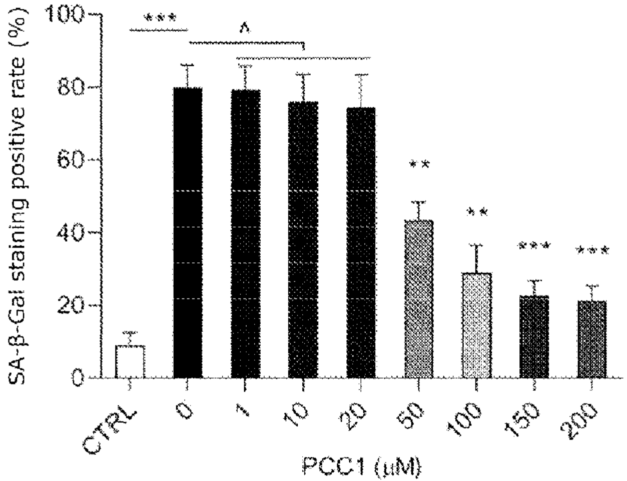
FIG. 12 shows whether PSC27 is senescent or not according to the determination by SA-β-Gal staining under the condition of increasing PCC1 concentration. ^, P>0.05; , P<0.01; **, P<0.0001, in which the P value for PCC1 at the concentrations of 1 μM, 10 μM, 20 μM, 50 μM, 100 μM, 150 μM and 200 μM is the statistical significance obtained by comparing the positive proportion of cells in these experimental groups with the data at 0 μM.
Figure 13:
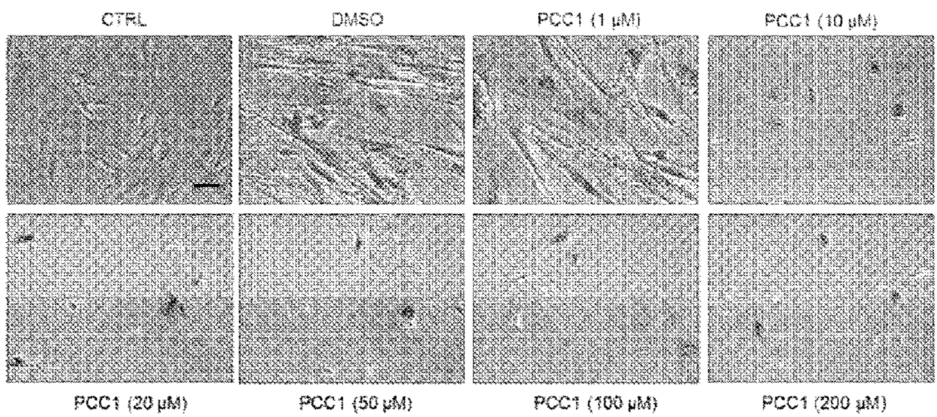
FIG. 13 shows the representative pictures of PSC27 under various conditions after SA-β-Gal staining. 3 repetitions per group, arranged up and down. Scale bar, 30 μm.

Given the remarkable efficacy of PCC1 in controlling SASP expression, we next explored the potential of this natural product to kill senescent cells at higher concentrations. To this end, we measured the percentage survival of treated senescent cells under in vitro conditions with increasing concentrations of PCC1. SA-β-Gal staining data indicated that senescent cells were not eliminated until the PCC1 concentration reached 50 μM (FIG. 12). As the concentration increased, the killing effect of PCC1 on senescent cells (80% staining positive) was further enhanced, and a threshold was reached when PCC1 was 150 μM (20% of senescent cells remained at this time); when its concentration was increased to 200 μM, the killing effect of PCC1 was not further enhanced (FIG. 12; FIG. 13).

Figure 14:
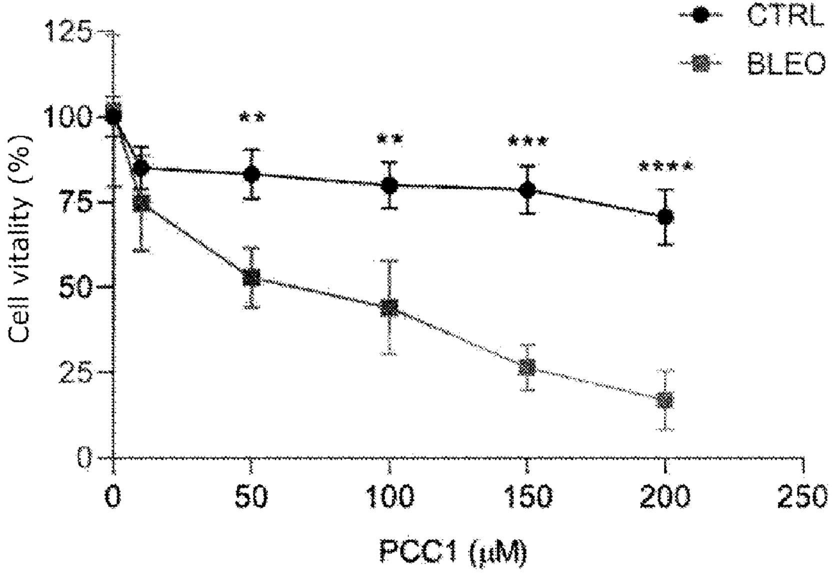
FIG. 14 shows that CCK8 detects the survival rates of proliferating cells and cells in the senescent group under increasing concentrations of PCC1. P value at each PCC1 concentration is the significant difference after comparison between CTRL and BLEO groups. , P<0.01; *, P<0.001; ****, P<0.0001.

To further dissect these issues, we conducted confirmatory experiments. Cell viability assays showed that PCC1 induced significant death of senescent cells starting from a concentration of 50 μM as compared to the corresponding control proliferating cells (FIG. 14). When the PCC1 concentration was increased to 200 11M, the percentage of surviving senescent cells decreased to approximately 10%. However, even at 200 μM of PCC1, proliferating cells were not significantly reduced. These results confirmed the high selectivity and outstanding specificity of PCC1 to senescent cells, and this feature was actually the basic technical requirement for senolytics as a unique class of anti-senescence drugs in the world.

Figure 15:
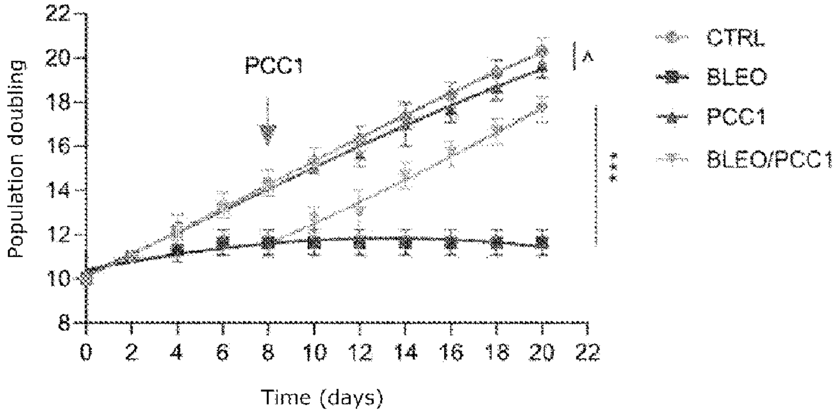
FIG. 15 shows the population doubling test of PSC27. The cells were damaged by BLEO at passage 10 (p10), and then PCC1 was added to the medium at day 8. The effect of PCC1 on cell proliferation potential is determined by comparative analysis of the population doubling (PD) of CTRL group, BLEO group, PCC1 group and BLEO/PCC1 group. ^, P>0.05; ***, P<0.001.

We next investigated the population doubling (PD) potential of stromal cells following genotoxic treatment. Compared with the cells of the BLEO group that entered a state of growth arrest rapidly after injury treatment, those of the combined BLEO and PCC1 treatment group showed a significantly increased PD ability (FIG. 15). Interestingly, however, PCC1 itself did not appear to affect the PD of proliferating cells, and the data further indicated the selectivity of PCC1 between senescent cells and normal cells.

Figure 16:
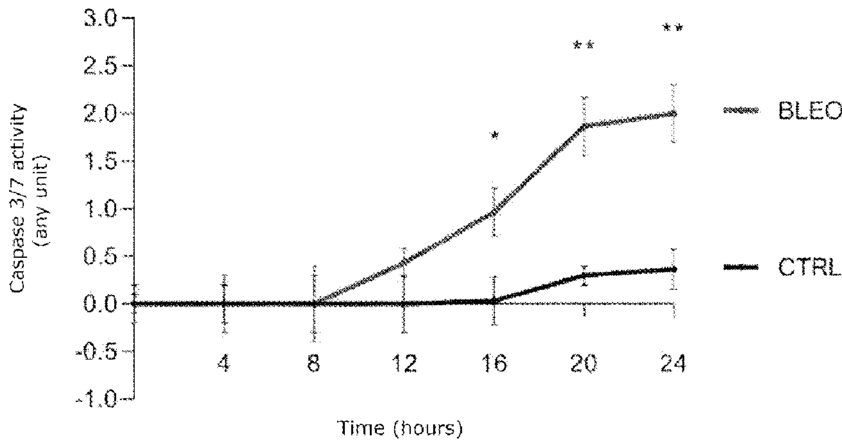
FIG. 16 shows that the caspase 3/7 activity was induced during the PCC1 treatment of senescent cells. PSC27 cells gradually entered the senescent stage after being treated with BLEO for 12 hours under culture conditions. 50 μM PCC1 was added to the medium of senescent cells starting from day 7, NucLight Rapid Red reagent was used to label the cells, and caspase 3/7 reagent (IncuCyte) was used for apoptosis detection. Caspase 3/7 activity was detected every 4 hours (n=3).
Figure 17:
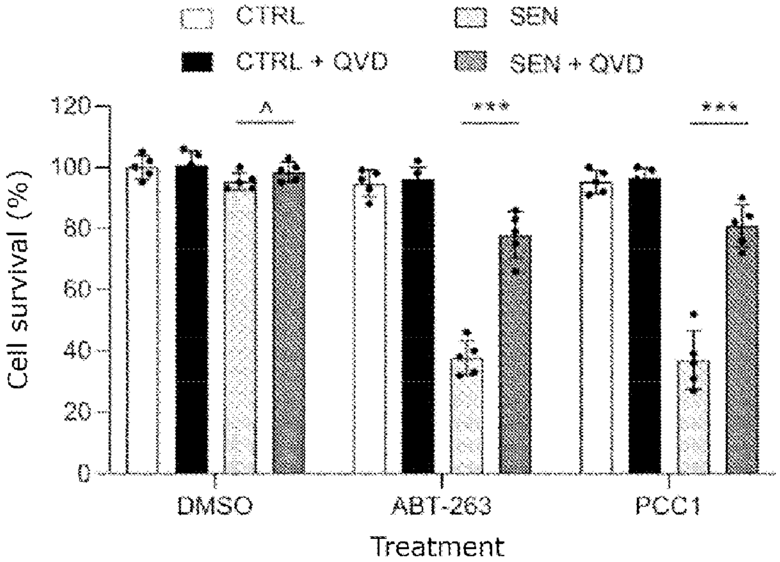
FIG. 17 shows the senolytic activity reversed by pan-caspase inhibitor (20 cM QVD-OPh) (50 μM PCC1 was used in this experiment, and 200 μM ABT263 was used as a positive control; the latter is a senescent cell apoptosis inducer reported in recent years). Statistical differences are obtained by two-way ANOVA (Turkey' test).

In order to explore whether PCC1 caused senescent cells to lose their viability by inducing apoptosis, we used PCC1 to treat the proliferation group cells and the senescence group cells respectively under culture conditions. The subsequently observed changes in caspase-3/7 activity showed that PCC1 caused apoptosis of senescent cells; from the $16^{th}$ hour after the addition of PCC1, there was a statistical difference between the aging group and the control group (FIG. 16). In addition, the pan-caspase inhibitor QVD could prevent the killing of senescent cells by PCC1, and the actual effect in this process was very similar to the effect of ABT263 (a currently known and very effective inducer of apoptosis in senescent cells) on senescent cells (FIG. 17). The above series of results confirmed that PCC1 promoted senescent cells to enter the death program by inducing apoptosis, but proliferating cells were basically not targeted or affected by this natural drug.

Figure 18:
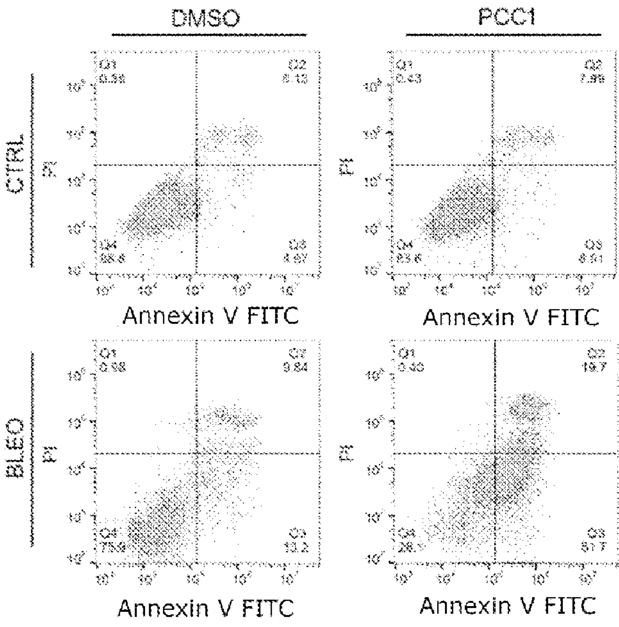
FIG. 18 shows the apoptosis of PSC27 under several conditions measured by flow cytometry. Q2, distribution area of early apoptotic cells; Q3, distribution area of late apoptotic cells.
Figure 19:
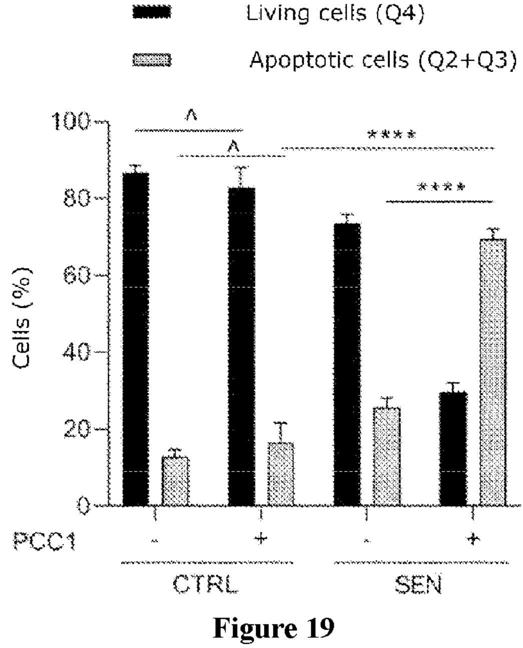
FIG. 19 shows the comparative analysis of the numbers of survival and apoptotic cells treated with BLEO and/or PCC1. *, P<0.001; **, P<0.0001.

Given the apparent effect of PCC1 on senescent cells, we then analyzed the potential of PCC1 to induce apoptosis. Flow cytometry data showed that the viability of senescent PSC27 cells was significantly reduced, while the proportion of apoptosis was significantly increased, but the change of proliferating cells was not obvious (FIG. 18; FIG. 19). Thus, the consistency of our data supported that PCC1 caused the elimination of senescent cells by inducing apoptosis in vitro and that this natural product had outstanding potential in targeting senescent cells.

Example 3: Use of PCC1 That Therapeutically Targets Senescent Cells to Promote Tumor Regression and Effectively Reduce Chemotherapy Resistance In view of the outstanding selectivity of PCC1 in clearing senescent cells at high concentrations in vitro, we next considered whether this drug could be used to intervene in various age-related diseases in vivo. Cancer is one of the major chronic diseases that seriously threaten human life and endanger health. In addition, drug resistance of cancer cells limits the effect of most anticancer treatments in clinic, and senescent cells often promote the occurrence of therapeutic drug resistance of surrounding cancer cells by developing SASP in damaged tumor foci. Even so, the feasibility and safety of removing senescent cells from primary tumors to promote a therapeutic index of cancer has been largely unexplored to date.

Figure 20:
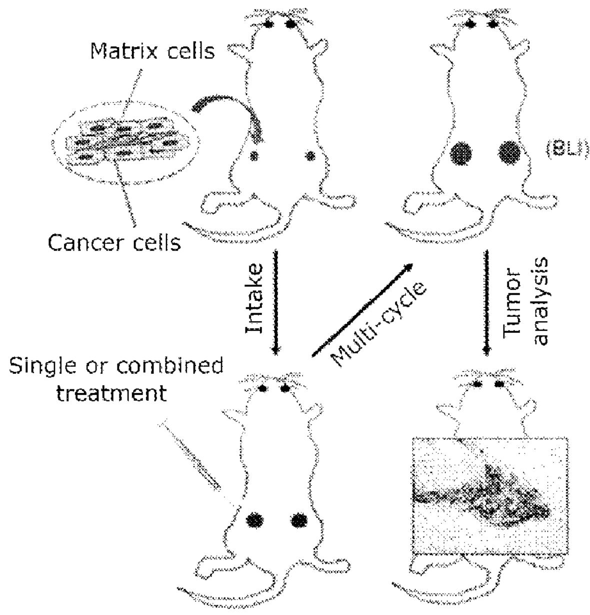
FIG. 20 shows a schematic diagram of the administration of mice in the preclinical trial. Human stromal cells PSC27 and cancer cells PC3 were mixed in vitro (1:4) and then transplanted into mice subcutaneously to form transplanted tumors. After multiple treatment cycles under the condition of single drug or combined drug administration, the mice were finally sacrificed, and the expression changes of relevant molecules in tumor tissues were analyzed pathologically.
Figure 21:
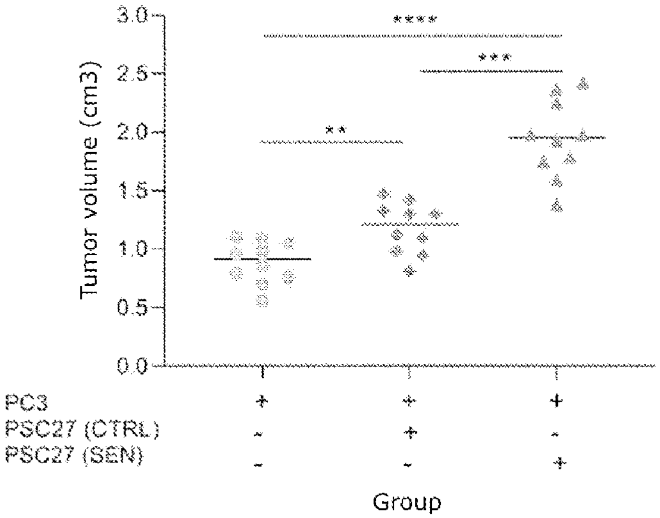
FIG. 21 shows that PC3 mixed with PSC27 cells of the CTRL group or BLEO injury group, or PC3 cells alone were transplanted into the subcutaneous tissue of mice to form transplanted tumors. At the end of the 8th week, the mice were dissected and the tumors were obtained, and the volumes of the tumors under the conditions of each group were detected and compared. , P<0.01; *, P<0.001; ****, P<0.0001.

First, we constructed tissue recombinant by mixing PSC27 stromal cells with PC3 epithelial cells, the latter is a typical highly malignant prostate cancer cell line. Before the recombinant was implanted subcutaneously in the posterior thigh of non-obese diabetic and severe combined immunodeficiency (NOD/SCID) mice, the ratio of stromal cells to epithelial cells was 1:4. Tumor size (volume) was measured at the end of 8 weeks after recombinant implantation in animals (FIG. 20). Compared with tumors composed of PC3 cancer cells and primary PSC27 stromal cells, the volumes of xenografts composed of PC3 cells and senescent PSC27 cells were significantly increased ($P<0.001$), this difference further confirmed the critical facilitative role of senescent cells in tumor progression (FIG. 21).

Figure 22:
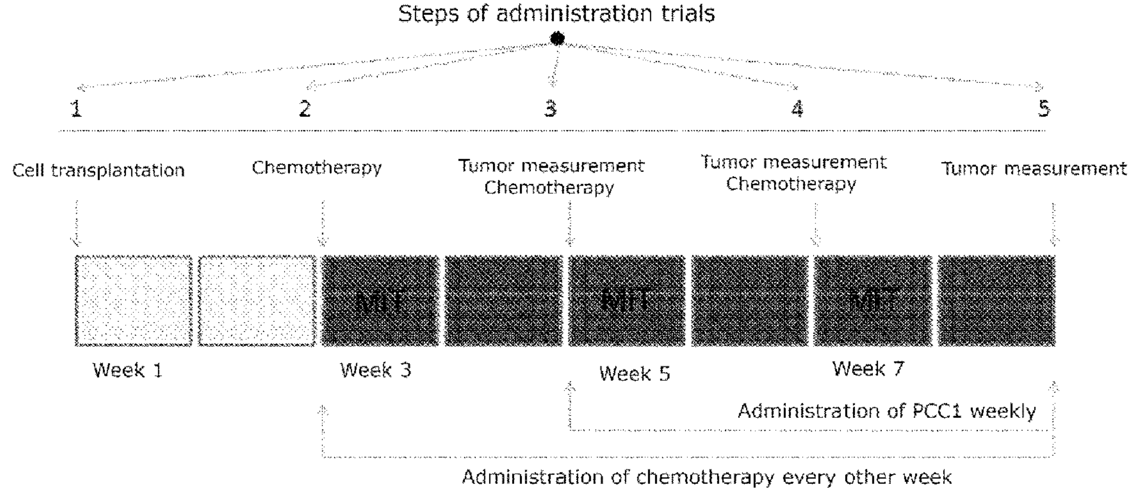
FIG. 22 shows a schematic diagram of the administration time and administration method for the mice in the preclinical trial. Every two weeks was a dosing cycle, and MIT (mitoxantrone) was intraperitoneally administered to the mice on the first day of the 3rd/5th/7th weeks. From the first day of the 5th week, the mice were intraperitoneally administrated with PCC1, once a week. After the 8-week course of treatment, the mice were dissected for pathological identification and expression analysis.
Figure 23:
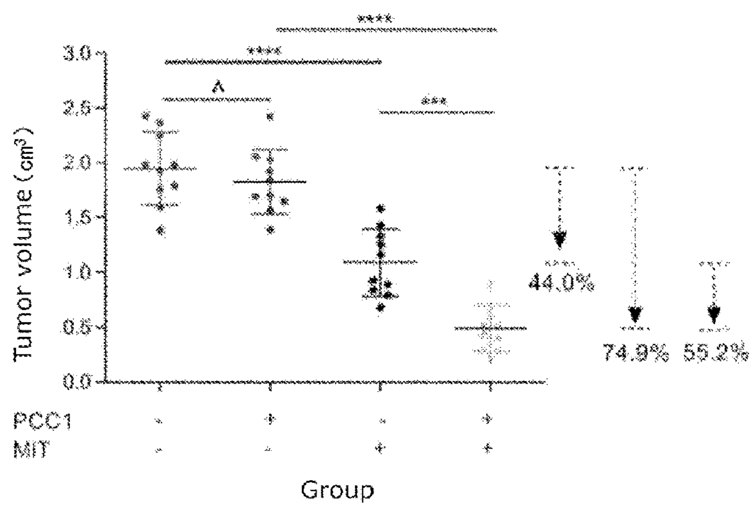
FIG. 23 shows the tumor terminal volume statistical analysis. Chemotherapeutic drug MIT alone or together with anti-senescence drug PCC1 was used to administer mice, and after the 8th week, the tumor size of each group was compared and analyzed.

To more closely approximate clinical conditions, we specifically designed a preclinical protocol involving genotoxic chemotherapeutic drug treatment and/or senescent drug intervention (FIG. 22). Two weeks after subcutaneous implantation, when stable tumor uptake in vivo was observed, we provided experimental animals with a single dose of MIT (Mitoxantrone, a chemotherapeutic agent) or placebo at the first day of the $3^{rd}$, $5^{th}$, $7^{th}$ weeks until the end of the 8 weeks regimen. MIT administration significantly delayed tumor growth compared to the placebo-treated group, that confirmed the efficacy of MIT as a chemotherapeutic agent (44.0% reduction in tumor size, $P<0.0001$) (FIG. 23). Notably, although PCC1 itself did not cause tumor shrinkage, the administration of PCC1 significantly reduced tumor size in mice treated with MIT (55.2% reduction in tumor volume compared with MIT, $P<0.001$; 74.9% reduction in tumor volume compared with placebo treatment, $P<0.0001$) (FIG. 23).

Figure 24:
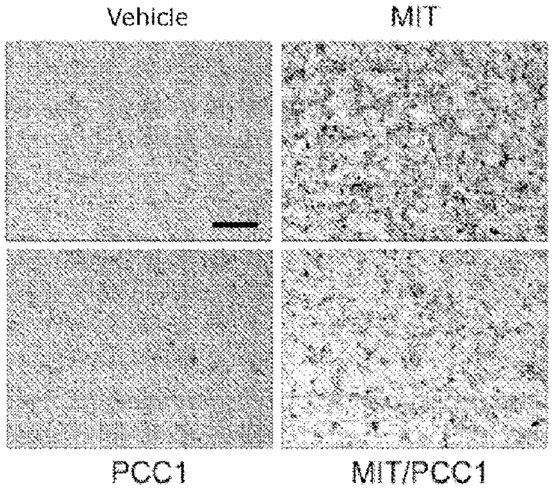
FIG. 24 shows the comparison of cell senescence in PC3/PSC27 tumor-bearing animal lesions in preclinical experiments. Representative pictures after SA-β-Gal staining. Scale bar, 100 μm.
Figure 25:
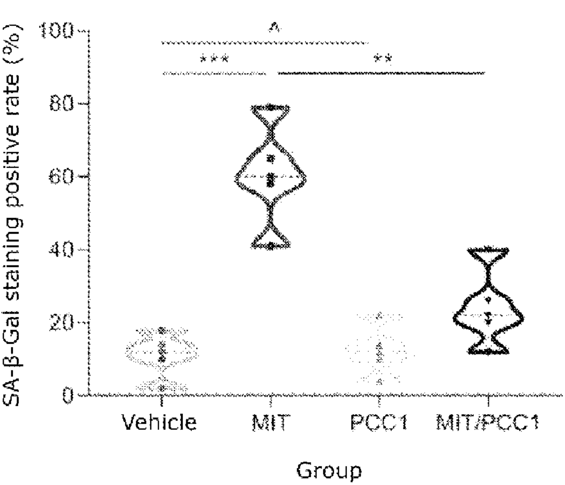
FIG. 25 shows the parallel analysis of the percentage of positive cells stained by SA-β-Gal in tumor tissues in mice. A P>0.05; , P<0.01; *, P<0.001.
Figure 26:
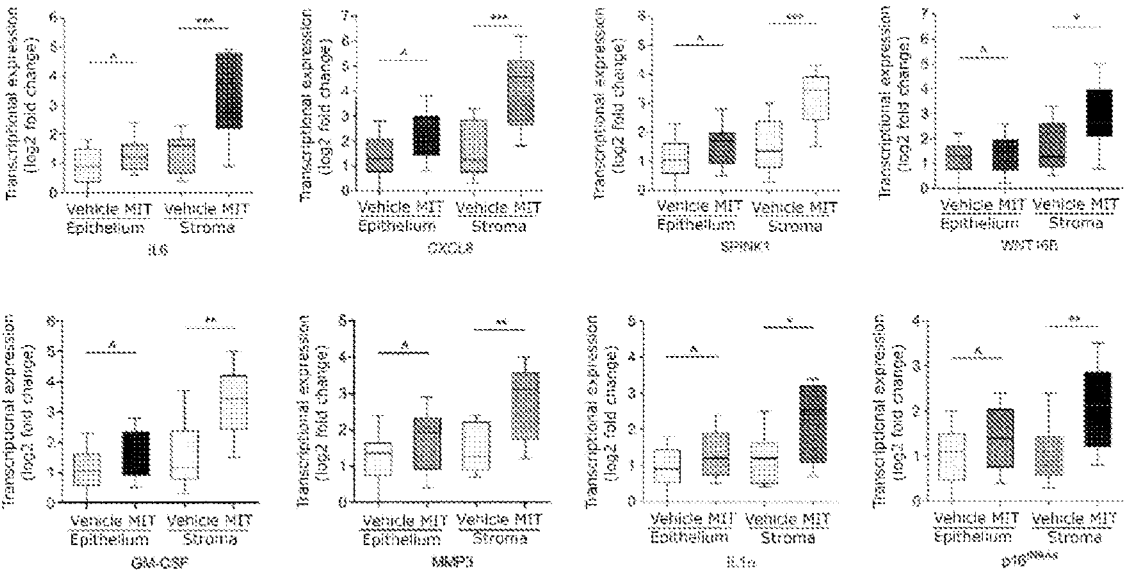
FIG. 26 shows the expression of SASP typical factors in epithelial cancer cells and stromal cells in mice lesions detected and analyzed by fluorescence quantitative PCR (qRT-PCR). The stromal cells and cancer cells were specifically separated by LCM technology, total RNA was prepared and used for SASP expression detection. A P>0.05; *, P<0.05; , P<0.01; *, P<0.001.
Figure 27:
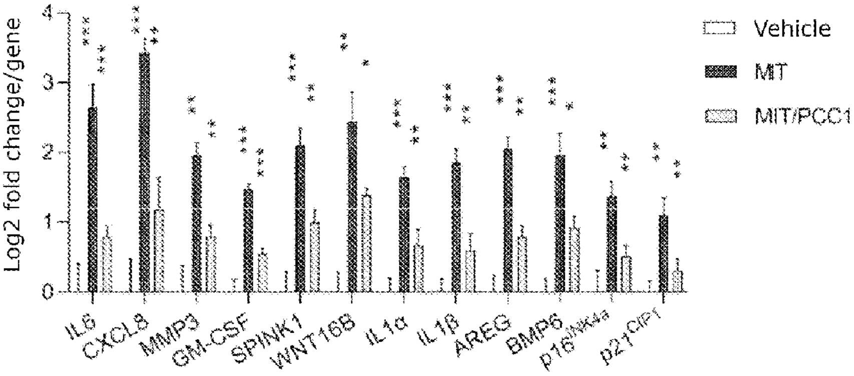
FIG. 27 shows the expression of SASP factors in the stromal cells in mice lesions administered with vehicle, MIT and MIT/PCC1 detected and analyzed by fluorescence quantitative PCR (qRT-PCR). *, P<0.05; , P<0.01; *, P<0.001.

We next inferred whether cell senescence occurred in tumor lesion in these animals. The test results proved that the MIT administration process induced the appearance of a large number of senescent cells in the tumor tissue, although this was not surprising. However, PCC1 administration substantially depleted most senescent cells within the lesions of these chemotherapeutic animals (FIG. 24; FIG. 25). Results of laser capture microdissection (LCM) and subsequent quantitative PCR revealed significantly elevated expression of SASP factors, including IL6, CXCL8, SPINK1, WNT16B, GM-CSF, MMP3, IL1α, and this trend accompanied with the up-regulation of senescence marker $p16^{INK4A}$ in chemotherapeutic animals (FIG. 26). Interestingly, these changes occurred mainly in stromal cells, but not in their adjacent cancer cells, implying the possibility of repopulation of residual cancer cells, the residual cancer cells had developed acquired resistance in the treatment-damaged tumor microenvironment (TME). However, this change was largely reversed when PCC1 was administered, as demonstrated by analysis of transcript-level data (FIG. 27).

Figure 28:
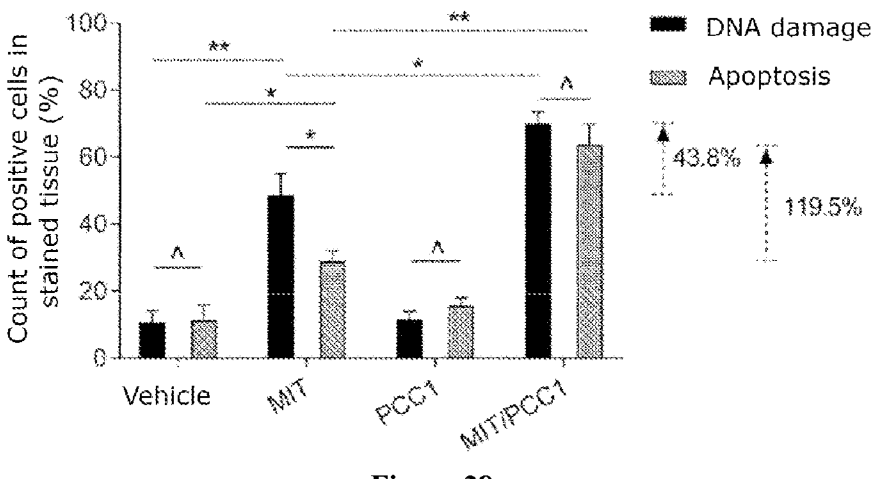
FIG. 28 shows that the ratio of DNA damage and apoptosis in mice of each group was analyzed after specific separation of cancer cells in the lesion by LCM technology. ^, P>0.05; *, P<0.05; ** P<0.01.
Figure 29:
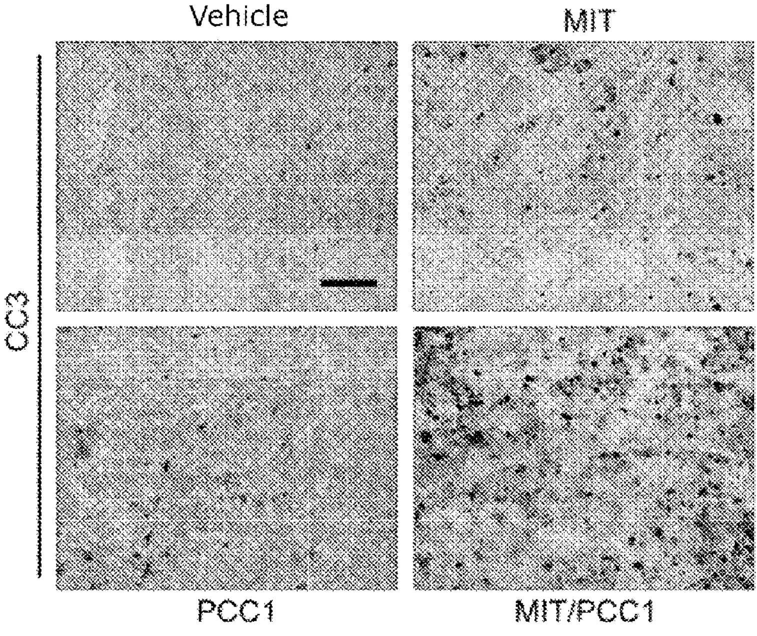
FIG. 29 shows the image analysis after immunohistochemical staining. The signals of Caspase 3 cleaved (CCL3) in the lesion of each group of mice were in sharp contrast. Scale bar, 200 μm.

To investigate mechanisms directly supporting this senescence-associated pattern with expression and reversal of SASP in MIT-administered mice, we dissected tumors in animals treated with both drugs 7 days after the first PCC1 administration, and the time point of 7 days after administration was selected mainly because drug-resistant clones had not yet formed in cancer cells in the lesion at this time. MIT administration resulted in a significant increase in both the degree of DNA damage and apoptosis compared with placebo. Although PCC1 alone could not induce DNA damage or cause apoptosis, the chemotherapeutic drug MIT could highly up-regulate these two indicators (FIG. 28). However, when MIT-treated animals were administered with PCC1, the indices of DNA damage or apoptosis were significantly enhanced, implying the enhanced cytotoxicity at tumor sites in these senescent drug-treated animals. As supporting evidence, when PCC1 was applied during treatment, caspase 3 cleavage activity was increased, which was a typical hallmark of apoptosis (FIG. 29).

Figure 30:
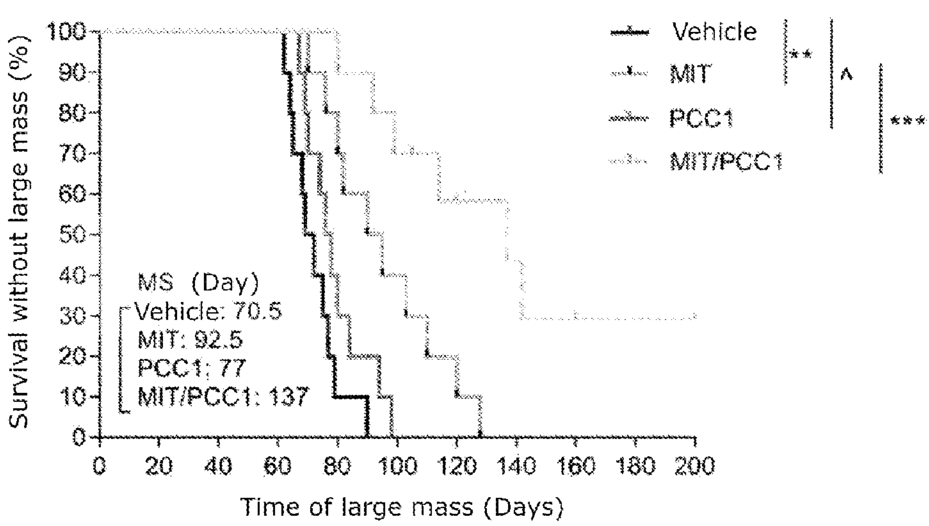
FIG. 30 shows the comparison of Kaplan Meier data of disease-free survival in NOD/SCID mice after various drug treatments. When the tumor volume in the vehicle, MIT, PCC1 and MIT/PCC1 groups exceeds 2000 $mm^3$, it is considered that severe disease has occurred, and the mice need to be killed in time and the tumor bearing status should be detected. ^, P>0.05; **, P<0.01.

We next compared the survival of animals in different drug-treated groups, primarily in a time-prolonged manner to assess the consequences of tumor progression. In this preclinical cohort, animals were monitored for prostate tumor growth, and severe disease was judged to have occurred once the endosomal tumor burden in mice was prominent (size ≥2000 $mm^3$), which was a method used for assessing progression of tumors and other diseases in certain conditions. The mice treated with the MIT/PCC1 combination exhibited the longest median survival, prolonging the survival by at least 48.1% compared to the group treated with MIT alone (FIG. 30, green versus blue). However, treating tumor-bearing mice with PCC1 alone did not result in a significant benefit, with only a marginal extension of survival.

Figure 31:
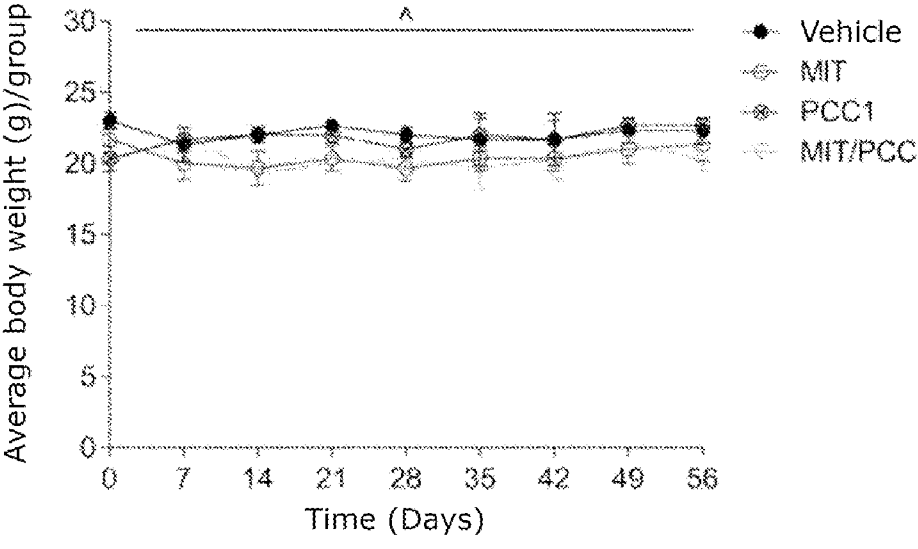
FIG. 31 shows the comparative analysis of the mice body weight data at the end of the course of treatment under various administration conditions. ^, P>0.05.
Figure 32:
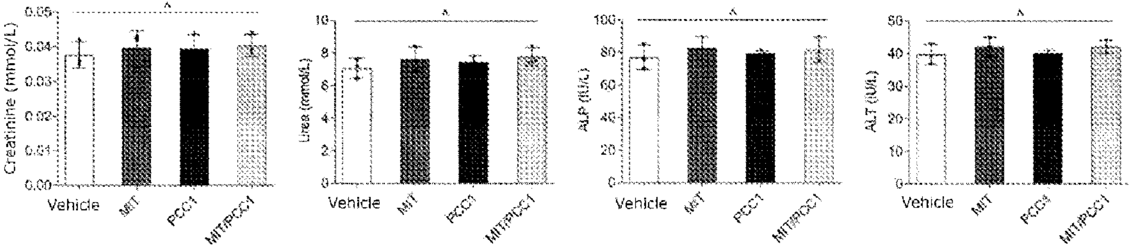
FIG. 32 shows the comparative analysis of the mice serological data at the end of the course of treatment under the above various administration conditions. Creatinine, urea (kidney indicator), ALP and ALT (liver indicator) data were compared in parallel. ^, P>0.05.
Figure 33:
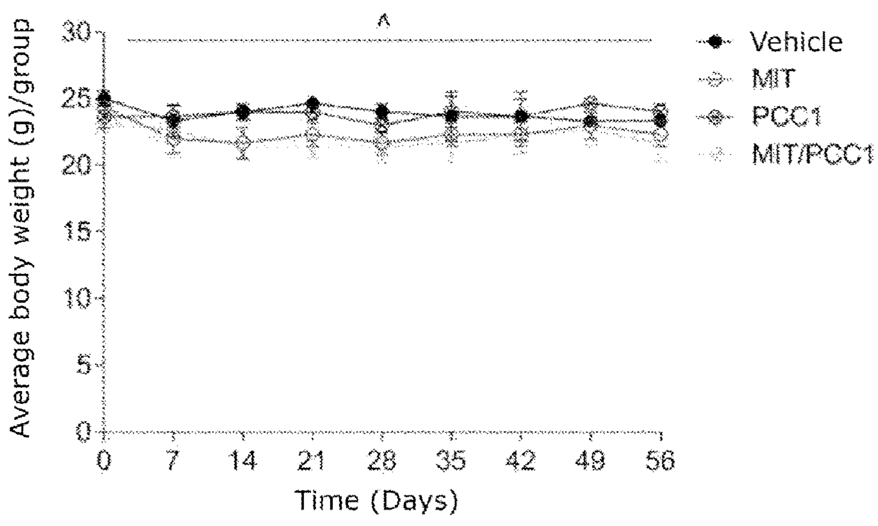
FIG. 33 shows the comparative analysis of body weight data of immune intact mice (C57BL/6J) at the end of the course of treatment under various administration conditions. ^, P >0.05.
Figure 34:
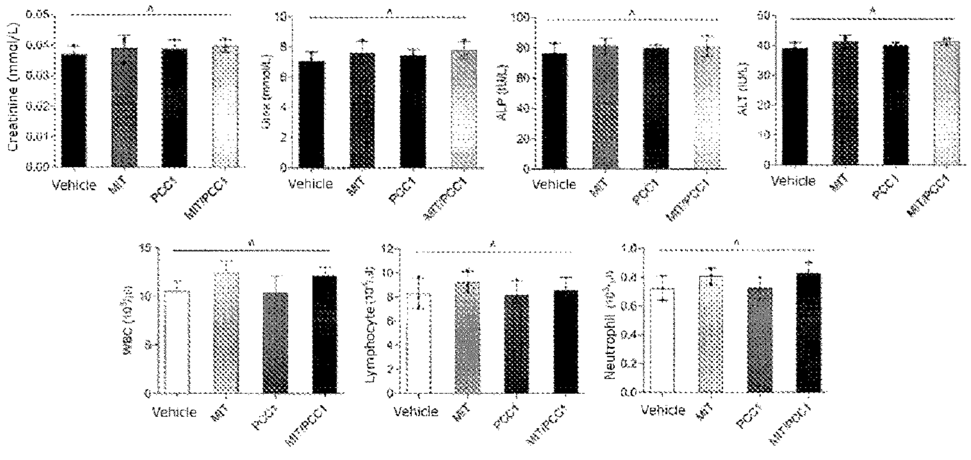
FIG. 34 shows the comparative analysis of mouse blood cell counts at the end of the course of treatment under various administration conditions in the preclinical trial. WBC, lymphocytes and neutrophils were compared in parallel. ^, P>0.05.

Remarkably, the treatments administered in these studies appeared to be well tolerated by the experimental mice. We did not observe significant fluctuations in urea, creatinine, alkaline phosphatase, glutamic-pyruvic transaminase, or body weight (FIG. 31; FIG. 32). More importantly, chemotherapy and anti-senescence drugs used at each drug dose designed for this study did not significantly interfere with the integrity of the immune system and tissue homeostasis of key organs, even in immunocompetent wild-type mice (FIG. 33; FIG. 34). These results consistently demonstrate that the combination of anti-senescence agents with conventional chemotherapeutic agents has the potential to enhance tumor response in a general sense without causing severe systemic toxicity.

Figure 35:
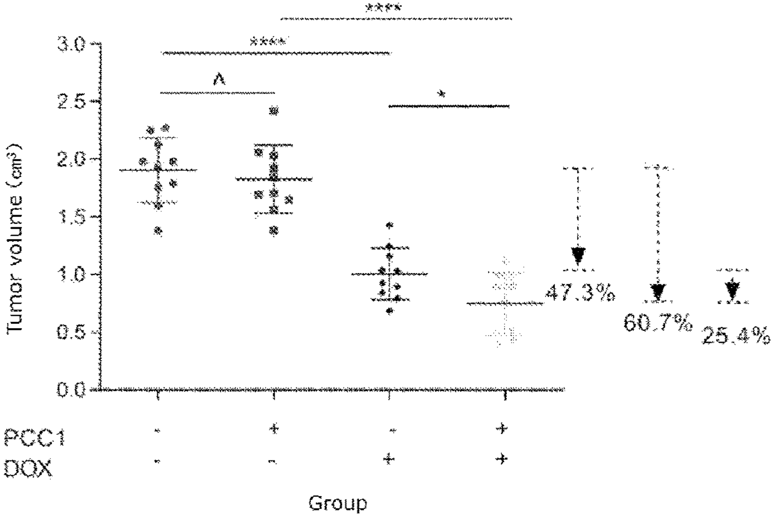
FIG. 35 shows the tumor terminal volume statistical analysis. Chemotherapeutic drug DOX alone or together with anti-senescence drug PCC1 was administered to mice, and the tumor size of each group was compared and analyzed after the end of the 8th week.
Figure 36:
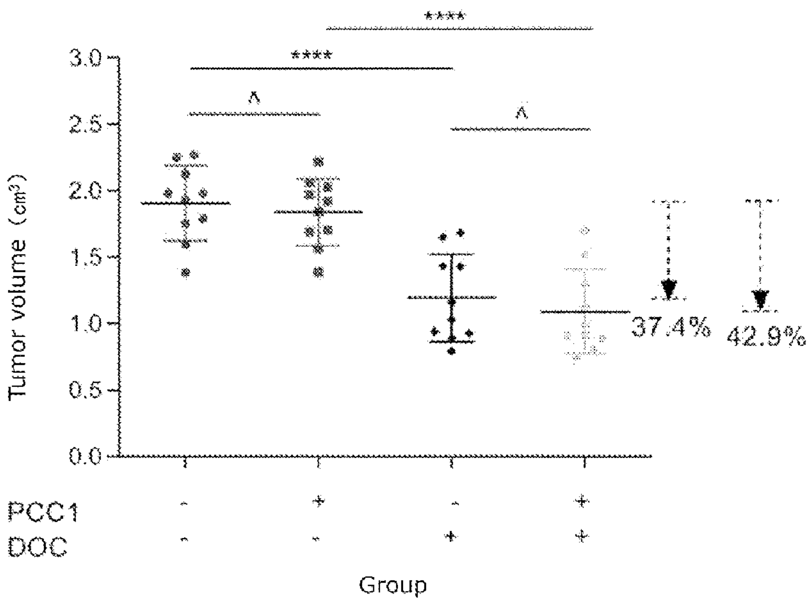
FIG. 36 shows the tumor terminal volume statistical analysis. Chemotherapeutic drug DOC alone or together with anti-senescence drug PCC1 was administered to mice, and the tumor size of each group was compared and analyzed after the end of the 8th week.
Figure 37:
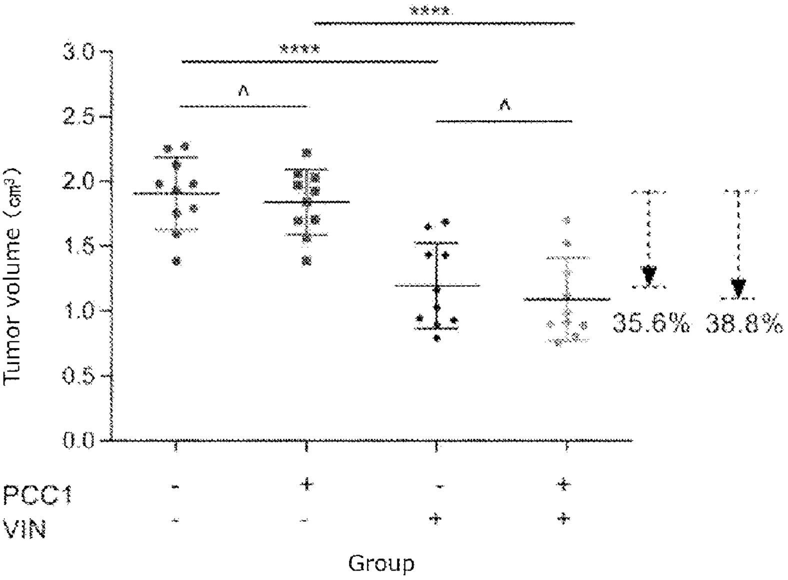
FIG. 37 shows the tumor terminal volume statistical analysis. Chemotherapeutic drug VIN alone or together with anti-senescence drug PCC1 was administered to mice, and the tumor size of each group was compared and analyzed after the end of the 8th week.

In order to determine whether PCC1 was drug-dependent or specific in improving the effect of chemotherapy, we then chose to use doxorubicin (DOX), docetaxel (DOC) and vincristine (VIN) to combine with PCC1 respectively for preclinical trials. The results showed that among these chemotherapeutic drugs, only the combination of DOX and PCC1 could roughly repeat the significant effect caused by the combined treatment of MIT and PCC1 (FIG. 35). However, although DOC and VIN could reduce the tumor volume when used alone, no further tumor shrinkage achieved when any one of DOC and VIN was administered together with PCC1, that was, no more benefits can be realized (FIG. 36, FIG. 37). Both MIT and DOX are genotoxic drugs, which can cause typical DNA double-strand breakage, and then cause cell senescence. The mechanism of action of VIN is to attach to microtubules and inhibit the process of mitosis. Therefore, the characteristic of PCC1 to improve the therapeutic effect of chemotherapy under in vivo conditions can be used in combination with drugs that induce the body to produce senescent cells, showing a drug-type dependence.

Figure 38:
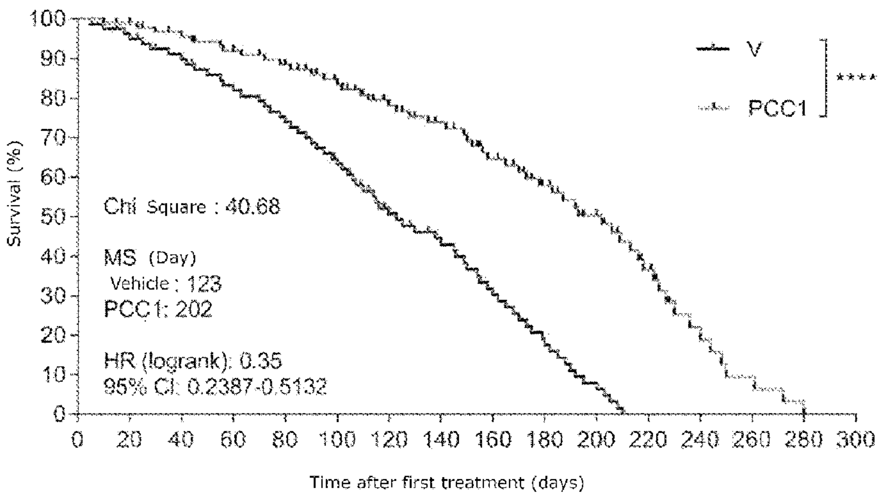
FIG. 38 shows the post-treatment survival curves for preclinical stage mice. Starting at 24 to 27 months of age, C57BL/6 mice received intraperitoneal administration of vehicle or PCC1 every two weeks (n=80 for vehicle group; n=91 for PCC1 group). The median survival of animals in each group was calculated and indicated. ****, P<0.0001.
Figure 39:
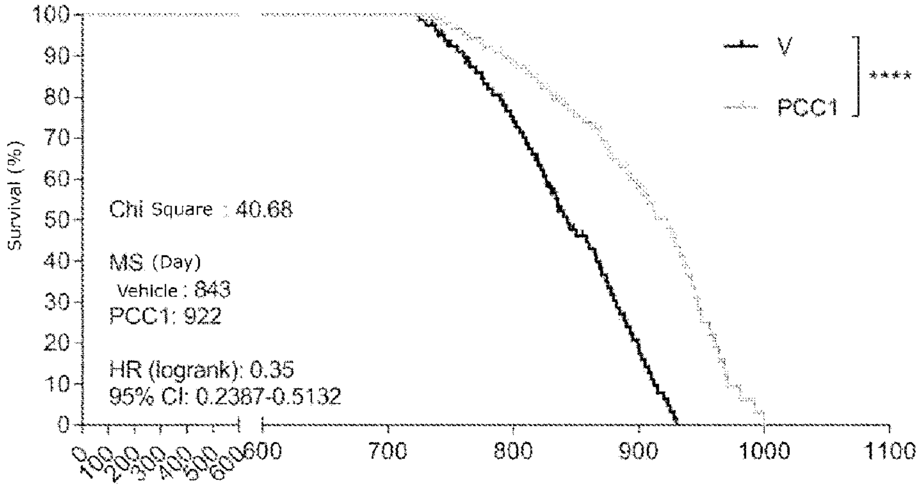
FIG. 39 shows the overall (lifetime, or full length) survival curves for preclinical stage mice. Starting at 24 to 27 months of age, C57BL/6 mice received intraperitoneal administration of vehicle or PCC1 every two weeks (n=80 for vehicle group; n=91 for PCC1 group). The median lifetime survival of animals in each group was calculated and indicated. ****, P <0.0001.

Example 4: Clearance of Senescent Cells By PCC1 Treatment Prolonging Late-life Survival in Aged Mice Without Increasing Morbidity in Late-life Stage Since PCC1 has the amazing efficacy of clearing senescent cells, reducing tumor drug resistance and improving the overall therapeutic effect in the microenvironment of tumor mice, is there also some significant benefit in promoting health or delaying disease in naturally aging animals? To answer this question, we first considered whether a potentially translational approach could be used to eliminate senescent cells, that was, intermittent treatment from a very old point in time whether extend the remaining lifespan of WT mice? In this regard, a series of in vivo experiments were carried out accordingly. It was worth noting, and quite surprising, that in the PCC1 group administered from the age of 24-27 months (equivalent to the age of 75-90 years in humans) under the regimen of taking the drug every two weeks, the median survival period after treatment was 64.2% longer than that of the vehicle group, and it had a lower risk of death (HR=0.35, PCC1 group/vehicle group; P<0.0001) (FIG. 38, FIG. 39). This finding suggests that PCC1-mediated clearance of senescent cells can reduce the risk of death in aged mice and effectively prolong their survival.

Figure 40:
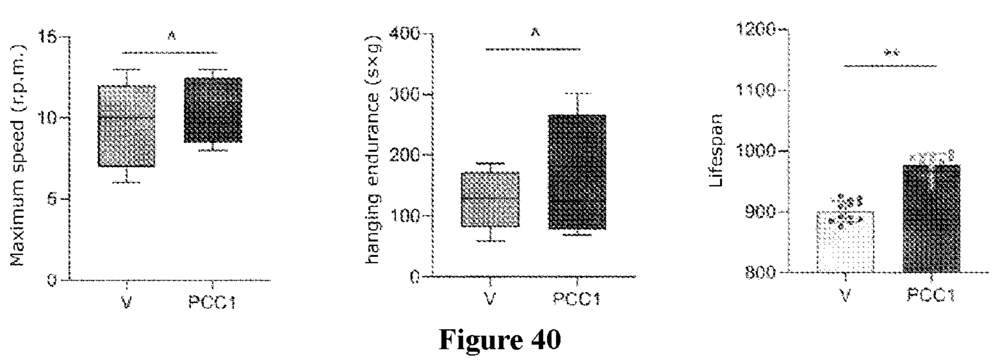
FIG. 40 shows that the female mice with the life length in the highest range among the animals in each group were selected for the comparative analysis of the highest walking speed, stamina and overall lifespan among the groups. N=5. ^, P>0.05; **, P<0.01.
Figure 41:
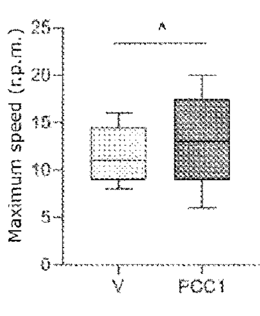
FIG. 41 shows that the male mice with the life length in the highest range among the animals in each group were selected for the comparative analysis of the highest walking speed, stamina and overall lifespan among the groups. N=5/group. , P>0.05; ***, P<0.001.
Figure 41:
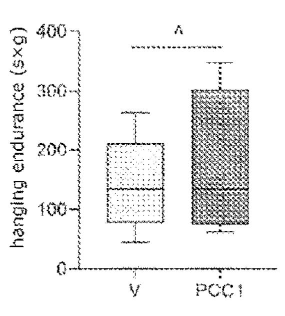
Figure 41:
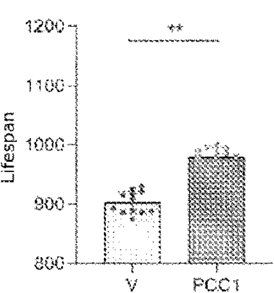
Figure 42:
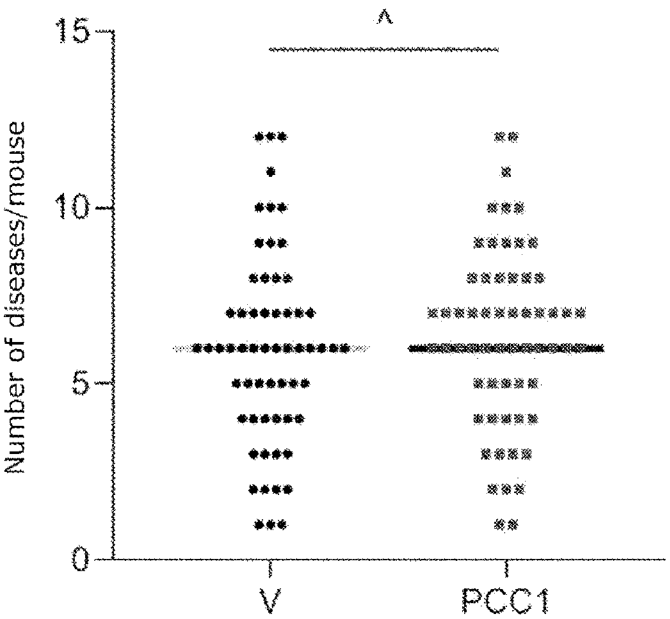
FIG. 42 shows the comparative analysis of the disease burden suffered by each mouse at the end of life in the two groups of animals. N=60/group. Statistical results are shown as box-and-whisker plots, each box shows the median with interquartile range. ^, P>0.05.
Figure 43:
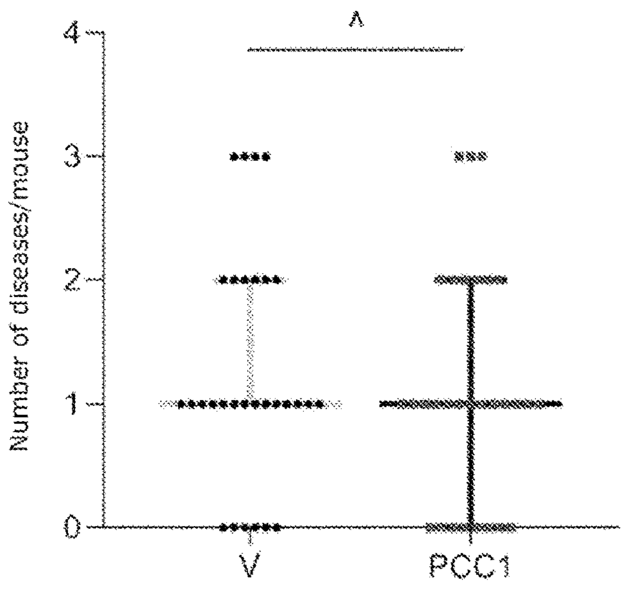
FIG. 43 shows the comparative analysis of the number of tumors developed in each mouse at the end of life in the two groups of animals. N=60/group. Statistical results are shown as box-and-whisker plots, each box shows the median with interquartile range. ^, P >0.05.

To further test whether this treatment regimen reduced mortality in aged mice at the expense of increased late morbidity, we assessed the physical function of these mice. Although the remaining lifespan of PCC1 group mice was longer, the mice treated with PCC1 biweekly did not show a significant decrease in physical function during the last 2 months of life as compared to the vehicle-treated group mice in both males and females (FIG. 40, FIG. 41). In addition, in the mouse autopsy, the prevalence of several age-related diseases and tumor burden did not show statistical differences between the two groups (FIG. 42, FIG. 43). Therefore, the intermittent supply of PCC1, a biologically active anti-senescence drug, could significantly reduce the disease burden of the aging body by clearing the senescent cells in the microenvironment, and could increase the lifespan of the body during post-treatment stage. That was, the subject of PCC1 administration did not have a significant change in the incidence of disease; once the body appeared certain senescence-related diseases (e.g., tumors), PCC1 could significantly improve the efficiency of tumor treatment or accelerate tumor regression. This treatment way did not lead to a significant increase in the body's morbidity, and could in reality be used safely in later stages of life.

What is claimed is:

1. A pharmaceutical composition, comprising (a) a procyanidin or a pharmaceutically acceptable salt, or hydrate thereof, and (b) an agent capable of inducing a subject to produce a senescent cell, and an optional pharmaceutically acceptable auxiliary material, wherein:

the procyanidin is procyanidin C1; and the agent is mitoxantrone (MIT).

2. The pharmaceutical composition according to claim 1, wherein:

the procyanidin or pharmaceutically acceptable salt, or hydrate thereof has a final concentration of at least 1 μM in the pharmaceutical composition.

3. A method for promoting tumor regression, reducing tumor size, treating a cancer, or prolonging cancer survival, comprising administering to a subject in need thereof an effective amount of a substance, wherein the substance comprises (a) a procyanidin or pharmaceutically acceptable salt, or hydrate thereof, and (b) an agent capable of inducing a subject to produce a senescent cell, wherein:

the tumor is a prostate tumor and/or the cancer is a prostate cancer;

the procyanidin is procyanidin C1; and the agent is mitoxantrone (MIT).

4. A medicine box or kit, wherein the medicine box or the kit comprises Container 1 and Container 2, which respectively contain (a) a procyanidin or a pharmaceutically acceptable salt, or hydrate thereof and an optional pharmaceutically acceptable auxiliary material, and (b) an agent capable of inducing a subject to produce a senescent cell and an optional pharmaceutically acceptable auxiliary material, wherein:

the procyanidin is procyanidin C1; and the agent is mitoxantrone (MIT).

* * * * *

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: IL6-F

<400> SEQUENCE: 1

ttctgcgcag ctttaaggag                                               20
```

-continued

<210> SEQ ID NO 2
<211> LENGTH: 20
<212> TYPE: DNA
<213> ORGANISM: Artificial Sequence
<220> FEATURE:
<223> OTHER INFORMATION: IL6-R

<400> SEQUENCE: 2
aggtgcccat gctacatttg 20

<210> SEQ ID NO 3
<211> LENGTH: 21
<212> TYPE: DNA
<213> ORGANISM: Artificial Sequence
<220> FEATURE:
<223> OTHER INFORMATION: CXCL8-F

<400> SEQUENCE: 3
atgacttcca agctggccgt g 21

<210> SEQ ID NO 4
<211> LENGTH: 20
<212> TYPE: DNA
<213> ORGANISM: Artificial Sequence
<220> FEATURE:
<223> OTHER INFORMATION: CXCL8-R

<400> SEQUENCE: 4
tgtgttggcg cagtgtggtc 20

<210> SEQ ID NO 5
<211> LENGTH: 20
<212> TYPE: DNA
<213> ORGANISM: Artificial Sequence
<220> FEATURE:
<223> OTHER INFORMATION: SPINK1-F

<400> SEQUENCE: 5
ccttggccct gttgagtcta 20

<210> SEQ ID NO 6
<211> LENGTH: 20
<212> TYPE: DNA
<213> ORGANISM: Artificial Sequence
<220> FEATURE:
<223> OTHER INFORMATION: SPINK1-R

<400> SEQUENCE: 6
gcccagattt ttgaatgagg 20

<210> SEQ ID NO 7
<211> LENGTH: 20
<212> TYPE: DNA
<213> ORGANISM: Artificial Sequence
<220> FEATURE:
<223> OTHER INFORMATION: WNT16B-F

<400> SEQUENCE: 7
gctcctgtgc tgtgaaaaca 20

<210> SEQ ID NO 8
<211> LENGTH: 20
<212> TYPE: DNA
<213> ORGANISM: Artificial Sequence
<220> FEATURE:

-continued

<223> OTHER INFORMATION: WNT16B-R

<400> SEQUENCE: 8
tgcattctct gccttgtgtc 20

<210> SEQ ID NO 9
<211> LENGTH: 20
<212> TYPE: DNA
<213> ORGANISM: Artificial Sequence
<220> FEATURE:
<223> OTHER INFORMATION: GM-CSF-F

<400> SEQUENCE: 9
atgtgaatgc catccaggag 20

<210> SEQ ID NO 10
<211> LENGTH: 20
<212> TYPE: DNA
<213> ORGANISM: Artificial Sequence
<220> FEATURE:
<223> OTHER INFORMATION: GM-CSF-R

<400> SEQUENCE: 10
agggcagtgc tgcttgtagt 20

<210> SEQ ID NO 11
<211> LENGTH: 20
<212> TYPE: DNA
<213> ORGANISM: Artificial Sequence
<220> FEATURE:
<223> OTHER INFORMATION: MMP3-F

<400> SEQUENCE: 11
agggaacttg agcgtgaatc 20

<210> SEQ ID NO 12
<211> LENGTH: 20
<212> TYPE: DNA
<213> ORGANISM: Artificial Sequence
<220> FEATURE:
<223> OTHER INFORMATION: MMP3-R

<400> SEQUENCE: 12
tcacttgtct gttgcacacg 20

<210> SEQ ID NO 13
<211> LENGTH: 20
<212> TYPE: DNA
<213> ORGANISM: Artificial Sequence
<220> FEATURE:
<223> OTHER INFORMATION: IL-1 alpha-F

<400> SEQUENCE: 13
aatgacgccc tcaatcaaag 20

<210> SEQ ID NO 14
<211> LENGTH: 20
<212> TYPE: DNA
<213> ORGANISM: Artificial Sequence
<220> FEATURE:
<223> OTHER INFORMATION: IL-1 alpha-R

<400> SEQUENCE: 14
tgggtatctc aggcatctcc 20

<210> SEQ ID NO 15
<211> LENGTH: 18
<212> TYPE: DNA
<213> ORGANISM: Artificial Sequence
<220> FEATURE:
<223> OTHER INFORMATION: p16INK4a-F

<400> SEQUENCE: 15
cttcctggac acgctggt 18

<210> SEQ ID NO 16
<211> LENGTH: 20
<212> TYPE: DNA
<213> ORGANISM: Artificial Sequence
<220> FEATURE:
<223> OTHER INFORMATION: p16INK4a-R

<400> SEQUENCE: 16
atctatgcgg gcatggttac 20

<210> SEQ ID NO 17
<211> LENGTH: 20
<212> TYPE: DNA
<213> ORGANISM: Artificial Sequence
<220> FEATURE:
<223> OTHER INFORMATION: IL-1 beta-F

<400> SEQUENCE: 17
tgggtatctc aggcatctcc 20

<210> SEQ ID NO 18
<211> LENGTH: 20
<212> TYPE: DNA
<213> ORGANISM: Artificial Sequence
<220> FEATURE:
<223> OTHER INFORMATION: IL-1 beta-R

<400> SEQUENCE: 18
ttctgcttga gaggtgctga 20

<210> SEQ ID NO 19
<211> LENGTH: 20
<212> TYPE: DNA
<213> ORGANISM: Artificial Sequence
<220> FEATURE:
<223> OTHER INFORMATION: AREG-F

<400> SEQUENCE: 19
agctgccttt atgtctgctg 20

<210> SEQ ID NO 20
<211> LENGTH: 20
<212> TYPE: DNA
<213> ORGANISM: Artificial Sequence
<220> FEATURE:
<223> OTHER INFORMATION: AREG-R

<400> SEQUENCE: 20
tttcgttcct cagcttctcc 20

<210> SEQ ID NO 21
<211> LENGTH: 20
<212> TYPE: DNA
<213> ORGANISM: Artificial Sequence
<220> FEATURE:
<223> OTHER INFORMATION: CXCL1-F

<400> SEQUENCE: 21
caccccaaga acatccaaag 20

<210> SEQ ID NO 22
<211> LENGTH: 20
<212> TYPE: DNA
<213> ORGANISM: Artificial Sequence
<220> FEATURE:
<223> OTHER INFORMATION: CXCL1-R

<400> SEQUENCE: 22
taactatggg ggatgcagga 20

<210> SEQ ID NO 23
<211> LENGTH: 20
<212> TYPE: DNA
<213> ORGANISM: Artificial Sequence
<220> FEATURE:
<223> OTHER INFORMATION: CXCL3-F

<400> SEQUENCE: 23
ggagcaccaa ctgacaggag 20

<210> SEQ ID NO 24
<211> LENGTH: 20
<212> TYPE: DNA
<213> ORGANISM: Artificial Sequence
<220> FEATURE:
<223> OTHER INFORMATION: CXCL3-R

<400> SEQUENCE: 24
cctttccagc tgtccctaga 20

<210> SEQ ID NO 25
<211> LENGTH: 20
<212> TYPE: DNA
<213> ORGANISM: Artificial Sequence
<220> FEATURE:
<223> OTHER INFORMATION: p21CIP1-F

<400> SEQUENCE: 25
atgaaattca cccccttcc 20

<210> SEQ ID NO 26
<211> LENGTH: 20
<212> TYPE: DNA
<213> ORGANISM: Artificial Sequence
<220> FEATURE:
<223> OTHER INFORMATION: p21CIP1-R

<400> SEQUENCE: 26
ccctaggctg tgctcacttc 20

<210> SEQ ID NO 27
<211> LENGTH: 20
<212> TYPE: DNA
<213> ORGANISM: Artificial Sequence
<220> FEATURE:
<223> OTHER INFORMATION: BMP6-F

<400> SEQUENCE: 27
aagaaggctg gctggaattt 20

<210> SEQ ID NO 28
<211> LENGTH: 20

-continued

```
<212> TYPE: DNA
<213> ORGANISM: Artificial Sequence
<220> FEATURE:
<223> OTHER INFORMATION: BMP6-R

<400> SEQUENCE: 28

gaagggctgc ttgtcgtaag                                                    20
```